(12) United States Patent
Tsimikas et al.

(10) Patent No.: US 7,939,287 B2
(45) Date of Patent: May 10, 2011

(54) METHODS OF IDENTIFYING A SUBJECT HAVING OR AT RISK OF HAVING OR DEVELOPING CORONARY ARTERY DISEASE

(75) Inventors: Sotirios Tsimikas, San Diego, CA (US); Joseph Witztum, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/465,930

(22) Filed: May 14, 2009

(65) Prior Publication Data

US 2009/0317819 A1 Dec. 24, 2009

Related U.S. Application Data

(60) Provisional application No. 61/053,146, filed on May 14, 2008.

(51) Int. Cl.
*C12Q 1/60* (2006.01)
(52) U.S. Cl. ............... 435/11; 435/6; 514/824
(58) Field of Classification Search ............... 435/11; 514/824
See application file for complete search history.

(56) References Cited

U.S. PATENT DOCUMENTS

| | | | |
|---|---|---|---|
| 2004/0071632 A1* | 4/2004 | Witztum et al. | 424/1.49 |
| 2004/0120893 A1* | 6/2004 | Witztum et al. | 424/1.49 |
| 2006/0177435 A1* | 8/2006 | Tsimikas et al. | 424/133.1 |
| 2008/0057590 A1* | 3/2008 | Urdea et al. | 436/71 |
| 2010/0160361 A1* | 6/2010 | Hislop et al. | 514/275 |

OTHER PUBLICATIONS

Kiechl S. et al. Oxidized Phospholipids, Lipoprotein(a), Lipoprotein Associated Phospholipase A2 Activity . . . Arteriosclerosis, Thrombosis and Vascular Biology 27(8)1788-1795, Aug. 2007.*
Tsimikas S. et al. New Insights Into the Role of Lipoprotein(a) Associated Lipoprotein Associated Phospholipase A2 . . . Arteriosclerosis Thrombosis and Vascular Biology 27(10)2094-2099, Oct. 2007.*
Libby P. et al. HDL-C Levels Predict CV Events Even When LDL-C is Low in Statin Treated Patients. Clinical Insights in Lipid Management1(4) Oct. 1-3, 2007.*
Ky B. et al. The Influence of Pravastatin and Atorvastatin on Markers of Oxidative Stress in Hypercholesterolemic Humans. J of American College of Cardiology 51(17)1653-62, Apr. 29, 2008.*

* cited by examiner

*Primary Examiner* — Ralph Gitomer
(74) *Attorney, Agent, or Firm* — Joseph R. Baker, Jr.; Gavrilovich Dodd & Lindsey LLP

(57) ABSTRACT

Provided herein are compositions and methods for identifying individuals at risk for developing coronary artery disease (CAD).

16 Claims, 8 Drawing Sheets

A

B

A

B

METHODS OF IDENTIFYING A SUBJECT HAVING OR AT RISK OF HAVING OR DEVELOPING CORONARY ARTERY DISEASE

CROSS REFERENCE TO RELATED APPLICATIONS

This application claims priority to U.S. Provisional Application Ser. No. 61/053,146, filed May 14, 2008, the disclosure of which is incorporated herein by reference.

STATEMENTS REGARDING FEDERALLY SPONSORED RESEARCH

The invention was made with government support under Grant No. HL56989 awarded by National Institutes of Health (NIH). The government has certain rights in the invention.

TECHNICAL FIELD

Compositions and methods for identifying individuals at risk for developing coronary artery disease (CAD) are provided.

BACKGROUND

The presence of chronic arterial inflammation in response to atherogenic stimuli has become a central tenet in explaining the development and destabilization of atherosclerotic plaques. Oxidized lipids play a central role in mediating a variety of immune, pro-inflammatory and plaque destabilizing processes that further amplify the inflammatory response. Underlying this inflammatory cascade is the production and secretion of cytokines, growth factors and metalloproteinases, such as interleukin-1 (IL-1), tumor necrosis factor alpha and C-reactive protein (CRP). Genetic variations in the IL-1 gene family (chromosome 2q13 region) commonly found in the human population can affect pro-inflammatory gene regulation and have been associated with elevated levels of pro-inflammatory mediators and increased risk for early cardiovascular events.

Oxidized phospholipids (OxPL) are present in atherosclerotic but not normal arteries. Plasma levels of specific OxPL on apolipoprotein B-100 (apoB) particles (OxPL/apoB) can be measured with the murine monoclonal antibody E06. OxPL/apoB levels are elevated in patients with coronary, carotid and femoral artery disease, acute coronary syndromes, and following percutaneous coronary intervention. Interestingly, in human plasma, OxPL are preferentially carried by Lp(a) lipoprotein (a) [Lp(a)], compared to other apoB-100 particles. Methods for determining the "atherogenesis index" (AI) (e.g., determining the ratio of OxPL/apoB) are provided in U.S. patent application Ser. No. 11/244,300 (Pub. No. 20060177435), which is incorporated herein by reference in its entirety.

SUMMARY

Provided herein are methods and compositions for determining a subject's predisposition to coronary artery disease, the method comprising: a) determining the subject's plasma OxPL level; b) determining lipoprotein-associated phospholipase A$_2$ (Lp-PLA$_2$) mass or activity, wherein increased levels of OxPL in association with increased Lp-PLA$_2$ mass or activity is indicative or a predisposition or risk of coronary artery disease. The method may further comprise c) determining the presence of a pro-inflammatory genotype in the IL-1 gene cluster of the subject and correlating a), b) and c) wherein a correlation provides additional predictive power for determining the predisposition or risk of coronary artery disease. In one embodiment, the OxPL is associated with apolipoprotein B-100 (apoB) particles. In another embodiment, the OxPL is associated with lipoprotein (a) (Lp(a)).

The disclosure demonstrates that measuring both the OxPL/apo-B level and Lp-PLA$_2$ mass or activity provides complimentary and synergistic information with a significant increase in the hazard ratio for predicting new cardiovascular events. Similarly, measuring lipoprotien (a) and the Lp-PLA$_2$ mass or activity and analyzing the data together provides similar information. Therefore, the disclosure allows one to determine a higher risk of new cardiovascular events by measuring simultaneously both the OxPL/apoB level and Lp-PLA2 mass and activity.

The disclosure also provides a high throughput assay to measure Lp-PLA$_2$ mass and activity on isolated Lp(a) particles or isolated apoB particles, rather than in plasma. Lp-PLA2 mass and activity are highly increased on Lp(a) particles, suggesting that this type of measure may be more predictive of future cardiovascular events. Currently there is no method to perform a high throughput assay to measure Lp-PLA$_2$ on Lp(a) particles. The disclosure provides a high throughput method that allows one to quickly capture Lp(a) or apoB-100 particles from the plasma in an in vitro assay and perform analysis looking at Lp-PLA2 mass and activity on captured Lp(a) or apoB-100 particles.

The disclosure also provides a markedly improved prediction power for new cardiovascular events by measuring both the OxPL/apoB level and the Lp-PLA$_2$ mass or activity in the same patient and allowing one to at least double the predictive power of the information. The information is useful for clinical prediction. The combination diagnostics of the disclosure provide a much more powerful predictor.

The disclosure also provides a diagnostic method that includes determining the IL-1 gene cluster genotype of the subject comprising a pro-inflammatory single nucleotide polymorphism in the IL-1A, IL-1B, or IL-1B gene, or any combination thereof. In some embodiment, the single nucleotide polymorphism in IL-1A is associated with the nucleotide at position +4845. In general the nucleotide at position +4845 is not G, but can be T. In another embodiment, the single nucleotide polymorphism in IL-1B is associated with the nucleotide at position +3954. In general the nucleotide at position +3954 is not C, but can be T. In another embodiment, the single nucleotide polymorphism in IL-1B is associated with the nucleotide at position −511. In general, the nucleotide at position −511 is not C, but can be T.

The disclosure also provides a kit for determining a subject's predisposition to coronary artery disease. The kit comprises (a) agents suitable for determining a subject's plasma OxPL level; (b) agents suitable for determining the nucleotide occurrences of pro-inflammatory SNPs associated with the IL-gene cluster; and (c) instructions for using the kit. In some aspects the agents suitable for determining a subject's plasma OxPL level are biomolecules such as antibodies. In other aspects, the agents suitable for determining the nucleotide occurrences of pro-inflammatory single nucleotide polymorphism (SNP) associated with the IL-gene cluster comprise oligonucleotide probes, primers, or primer pair, or combinations thereof, for identifying the nucleotide occurrence of at least one pro-inflammatory single nucleotide polymorphism (SNP).

The details of one or more embodiments of the disclosure are set forth in the accompanying drawings and the description below. Other features, objects, and advantages will be apparent from the description and drawings, and from the claims.

DETAILED DESCRIPTION

Figure 1:
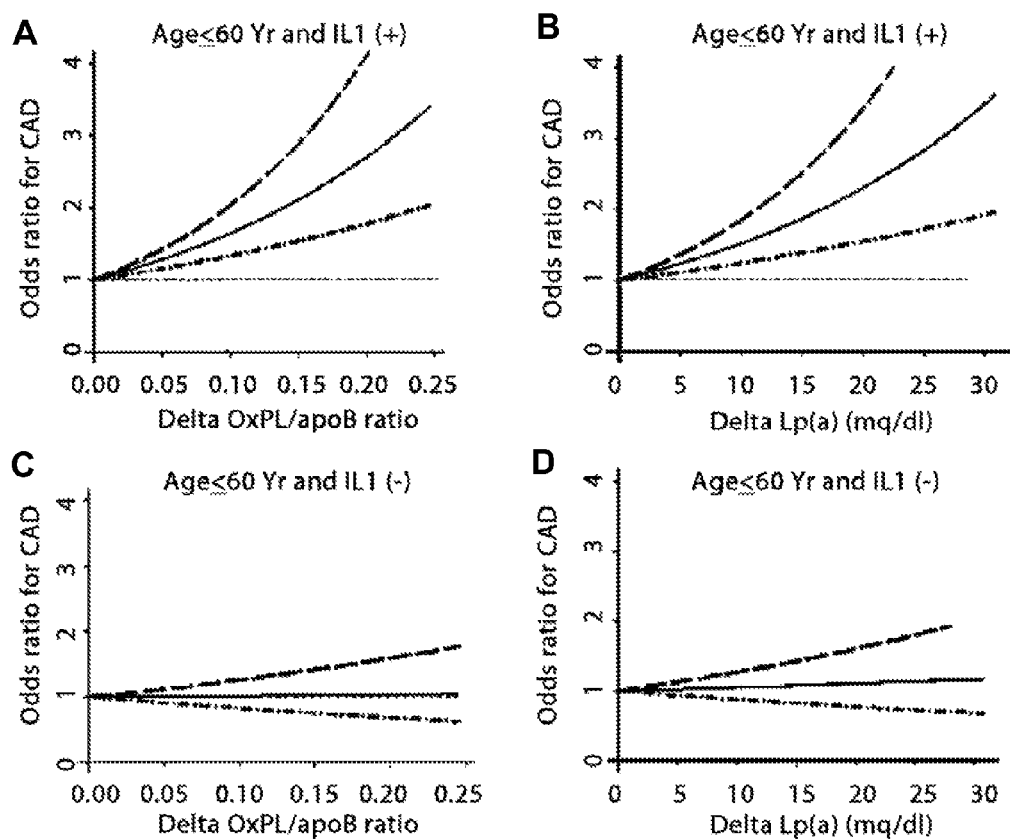
FIG. 1, panels A-D depict odds ratios (OR) (solid line) and 95% confidence intervals (dashed lines) for CAD were calculated in a logistic regression model. In this model, the delta OxPL/apoB and delta Lp(a) represent the difference in values between any 2 quartiles of OxPL/apoB or Lp(a) levels and the corresponding OR for CAD. The analysis was performed on patients $\leq 60$ years of age stratified as IL-1(+) or IL-1(−).

Before describing the invention in detail, it is to be understood that this invention is not limited to particular compositions or biological systems, which can, of course, vary.

As used herein and in the appended claims, the singular forms "a," "and," and "the" include plural referents unless the context clearly dictates otherwise. Thus, for example, reference to "a phospholipid" includes a plurality of such phospholipids and reference to "the protein" includes reference to one or more proteins, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

A "coronary artery disease" ("CAD") refers to a vascular disorder relating to the blockage of arteries serving the heart. Blockage can occur suddenly, by mechanisms such as plaque rupture or embolization. Blockage can occur progressively, with narrowing of the artery via myointimal hyperplasia and plaque formation. Those clinical signs and symptoms resulting from the blockage of arteries serving the heart are manifestations of coronary artery disease. Atherosclerosis (sometimes called "hardening" or "clogging" of the arteries) is the buildup of cholesterol and fatty deposits (called plaque) on the inner walls of the arteries that restricts blood flow to the heart. Acute Coronary Syndrome is a name given to three types of coronary artery disease that are associated with sudden rupture of plaque inside the coronary artery: unstable angina, Non-ST segment elevation myocardial infarction or heart attack (NSTEMI), or ST segment elevation myocardial infarction or heart attack (STEMI). The length of time that blood flow is blocked and the amount of damage that occurs determines the type of acute coronary syndrome. An acute coronary syndrome can be caused by a small plaque, not necessarily detected by stress testing or cardiac catheterization. Prior symptoms may or may not be present. Manifestations of coronary artery disease include angina, ischemia, myocardial infarction, cardiomyopathy, congestive heart failure, arrhythmias and aneurysm formation. It is understood that fragile plaque disease in the coronary circulation is associated with arterial thrombosis or distal embolization that manifests itself as a myocardial infarction. It is understood that occlusive disease in the coronary circulation is associated with arterial stenosis accompanied by anginal symptoms, a condition commonly treated with pharmacological interventions and with angioplasty.

A "cardiovascular disease" is a cardiovascular disorder, as defined herein, characterized by clinical events including clinical symptoms and clinical signs. Clinical symptoms are those experiences reported by a patient that indicate to the clinician the presence of pathology. Clinical signs are those objective findings on physical or laboratory examination that indicate to the clinician the presence of pathology. "Cardiovascular disease" includes both "coronary artery disease" and "peripheral vascular disease," both terms being defined below. Clinical symptoms in cardiovascular disease include chest pain, shortness of breath, weakness, fainting spells, alterations in consciousness, extremity pain, paroxysmal nocturnal dyspnea, transient ischemic attacks and other such phenomena experienced by the patient. Clinical signs in cardiovascular disease include such findings as EKG abnormalities, altered peripheral pulses, arterial bruits, abnormal heart sounds, rales and wheezes, jugular venous distention, neurological alterations and other such findings discerned by the clinician. Clinical symptoms and clinical signs can combine in a cardiovascular disease such as a myocardial infarction (MI) or a stroke (also termed a "cerebrovascular accident" or "CVA"), where the patient will report certain phenomena (symptoms) and the clinician will perceive other phenomena (signs) all indicative of an underlying pathology. "Cardiovascular disease" includes those diseases related to the cardiovascular disorders of fragile plaque disorder, occlusive disorder and stenosis. For example, a cardiovascular disease resulting from a fragile plaque disorder, as that term is defined below, can be termed a "fragile plaque disease." Clinical events associated with fragile plaque disease include those signs and symptoms where the rupture of a fragile plaque with subsequent acute thrombosis or with distal embolization are hallmarks. Examples of fragile plaque disease include certain strokes and myocardial infarctions. As another example, a cardiovascular disease resulting from an occlusive disorder can be termed an "occlusive disease." Clinical events associated with occlusive disease include those signs and symptoms where the progressive occlusion of an artery affects the amount of circulation that reaches a target tissue. Progressive arterial occlusion may result in progressive ischemia that may ultimately progress to tissue death if the amount of circulation is insufficient to maintain the tissues. Signs and symptoms of occlusive disease include claudication, rest pain, angina, and gangrene, as well as physical and laboratory findings indicative of vessel stenosis and decreased distal perfusion. As yet another example, a cardiovascular disease resulting from restenosis can be termed an in-stent stenosis disease. In-stent stenosis disease includes the signs and symptoms resulting from the progressive blockage of an arterial stent that has been positioned as part of a procedure like a percutaneous transluminal angioplasty, where the presence of the stent is intended to help hold the vessel in its newly expanded configuration. The clinical events that accompany in-stent stenosis disease are those attributable to the restenosis of the reconstructed artery.

A "cardiovascular disorder" refers broadly to both to coronary artery disorders and peripheral arterial disorders. The term "cardiovascular disorder" can apply to any abnormality of an artery, whether structural, histological, biochemical or any other abnormality. This term includes those disorders characterized by fragile plaque (termed herein "fragile plaque disorders"), those disorders characterized by vaso-occlusion (termed herein "occlusive disorders"), and those disorders characterized by restenosis. A "cardiovascular disorder" can occur in an artery primarily, that is, prior to any medical or surgical intervention. Primary cardiovascular disorders include, among others, atherosclerosis, arterial occlusion, aneurysm formation and thrombosis. A "cardiovascular disorder" can occur in an artery secondarily, that is, following a medical or surgical intervention. Secondary cardiovascular disorders include, among others, post-traumatic aneurysm formation, restenosis, and post-operative graft occlusion.

"Increased risk" refers to a statistically higher frequency of occurrence of the disease or disorder in an individual in comparison to the frequency of occurrence of the disease or disorder in a population. A factor identified to be associated with increased risk is termed a "risk factor." A ratio of OxPL/apoB and Lp-PLA2 activity that is increased are "risk factors". In addition, carrying a particular polymorphic allele is a risk factor for a particular cardiovascular disease, and is associated with an increased risk of the particular disease.

A "risk factor" is a factor identified to be associated with an increased risk. A risk factor for a cardiovascular disorder or a cardiovascular disease is any factor identified to be associated with an increased risk of developing those conditions or of worsening those conditions. A risk factor can also be associated with an increased risk of an adverse clinical event or an adverse clinical outcome in a patient with a cardiovascular disorder. Risk factors for cardiovascular disease include smoking, adverse lipid profiles, elevated lipids or cholesterol, diabetes, hypertension, hypercoagulable states, elevated homocysteine levels, increased Lp-$PLA_2$ and $sPLA_2$ activity, and lack of exercise. Carrying a particular polymorphic allele is a risk factor for a particular cardiovascular disorder, and is associated with an increased risk of the particular disorder.

For many years, epidemiologic studies have indicated that an individual's genetic composition is a significant risk factor for development of a vascular disease. For example, a family history of heart disease is associated with an increased individual risk of developing coronary artery disease. Lipid and cholesterol metabolism have historically been considered the primary genetic influence on coronary artery disease. For example, deficiency in cell receptors for low-density lipids (LDL), such as in familial hypercholesterolemia, is associated with high levels of plasma LDL and premature development of atherosclerosis (Brown & Goldstein, Sci., 191 (4223):150-4 (1976)).

A key problem in treating vascular diseases is proper diagnosis. Often the first sign of the disease is sudden death. For example, approximately half of all individuals who die of coronary artery disease die suddenly, Furthermore, for 40-60% of the patients who are eventually diagnosed as having coronary artery disease, myocardial infarction is the first presentation of the disease. Unfortunately, approximately 40% of those initial events go unnoticed by the patient.

Inflammation is now generally regarded as an important component of the pathogenic process of atherosclerosis (Munro, Lab Invest., 58:249-261 (1988); Badimon, et al., Circulation, 87:3-16 (1993); Liuzzo, et al., N.E.J.M., 331(7):417-24 (1994); Alexander, N.E.J.M., 331(7):468-9 (1994)). Several inflammatory products, including IL-1 beta, have been identified in atherosclerotic lesions or in the endothelium of diseased coronary arteries (Galea, et al., Ath. Thromb. Vasc. Biol., 16:1000-6 (1996)). Also, serum concentrations of IL-1 beta have been found to be elevated in patients with coronary disease (Hasdai, et al., Heart, 76:24-8 (1996)).

Oxidized phospholipids (OxPL) are pro-inflammatory and are detected by monoclonal antibody E06 on apolipoprotein B-100 particles (OxPL/apoB), and primarily on lipoprotein A (Lp(a)).

The disclosure demonstrates that OxPL/apoB measured at baseline in an unselected population derived from the general community predicts the development of cardiovascular events over a 10-year prospective follow-up period. The predictive value of OxPL/apoB was independent of traditional risk factors and hsCRP, and further amplified with increasing Lp-$PLA_2$ activity. Furthermore, elevated OxPL/apoB levels provided predictive information within each Framingham Risk Score estimate of 10-year cardiovascular risk. Similar findings were noted for Lp(a). OxPL/apoB and Lp(a) were not independent of each other but were independent of all other measured risk factors. The close relationship of OxPL/apoB and Lp(a) in predicting cardiovascular events strongly supports the hypothesis that the atherogenicity of Lp(a) may be due, in part, to its ability to preferentially bind pro-inflammatory oxidized phospholipids compared to other apoB-containing lipoproteins.

The OxPL/apoB assay quantitates the content of OxPL per apoB particle and was originally designed to measure minimally oxidized LDL in plasma. However, it was later determined that most, but not all, of the OxPL/apoB are actually a subset of apoB-100 particles, namely Lp(a) particles, and thus, this assay represents a novel biological measure of oxidized phospholipids that are primarily on Lp(a) particles. It is also noteworthy to emphasize that the term "OxLDL" is not a single molecular entity but describes a broad array of biological, chemical and immunological changes that result in generation of oxidation-specific epitopes. The antibodies and assays used for measuring OxLDL described in the literature are not necessarily comparable nor are they expected to provide similar results, primarily due to differences in epitope recognition and fundamentally different assay methodologies.

Lp(a) is associated with enhanced atherogenic potential, particularly at levels >30 mg/dl, and is shown to be an independent predictor (odds ratio –1.5-2) of cardiovascular risk, particularly in younger subjects (<60 years old) and those with elevated LDL cholesterol levels. Since it appears that the atherogenicity of Lp(a) may be mediated in part by its association with OxPL. This study also provides evidence that a J-shaped relationship may exist between Lp(a) levels and cardiovascular events. In the Scandinavian Simvastatin Survival Study, Berg et al. showed that subjects with elevated Lp(a) levels had a higher risk of death and major cardiac events, and interestingly, the greatest benefit with simvastatin was not derived in the lowest Lp(a) quartile, but in the next to lowest, which is consistent with the current data.

Lipoprotein Associated Phospholipase $A_2$ (Lp-PLA$_2$), also previously known in the art as Platelet Activating Factor Acetyl Hydrolase (PAF acetyl hydrolase) is responsible for hydrolysing the sn-2 ester of oxidatively modified phosphatidylcholine to give lyso-phosphatidylcholine and an oxidatively modified fatty acid. Both of these products of Lp-PLA$_2$ action are potent chemoattractants for circulating monocytes. As such, this enzyme is thought to be responsible for the accumulation of cells loaded with cholesterol ester in the arteries, causing the characteristic 'fatty streak' associated with the early stages of atherosclerosis. It is proposed that Lp-PLA$_2$ plays a direct role in LDL oxidation. This is due to the poly unsaturated fatty acid-derived lipid peroxide products of Lp-PLA$_2$ action contributing to and enhancing the overall oxidative process.

The disclosure demonstrates for the first time a relationship between OxPL and Lp-PLA$_2$ activity in predicting CVD. Higher baseline levels of Lp-PLA$_2$ activity were present in subjects with incident CVD, but primarily in studies measuring Lp-PLA$_2$ mass. Both OxPL/apoB and Lp-PLA$_2$ activity were significant predictors of vascular risk in multivariable models. However, the prediction of CVD by OxPL/apoB or Lp(a) was significantly accentuated by increasing Lp-PLA$_2$ activity (effect modification, P for interaction 0.018 and 0.008 for OxPL/apoB and Lp(a), respectively), but when either OxPL/apoB (or Lp(a)) and Lp-PLA$_2$ levels were low, there was essentially no association of either with CVD. This finding implies that these measures may be related pathophysiologically and provide complementary information in predicting new CVD events.

Figure 6:
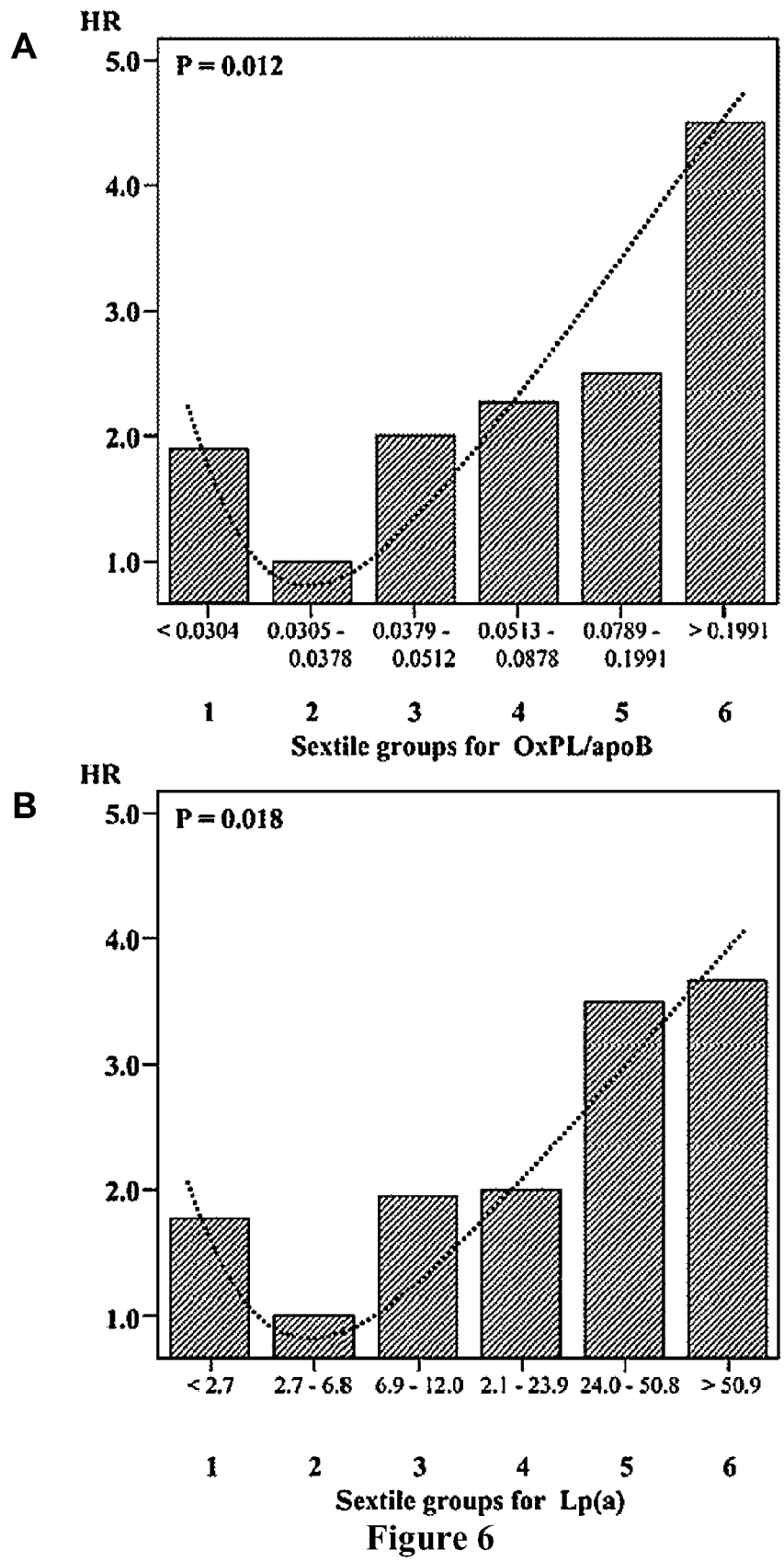
FIG. 6A-B shows plots of hazard ratios for incident CVD according to OxPL/apoB (A), and Lp(a) (B) sextile groups.

Animal studies of overexpression of Lp-PLA$_2$ suggest that it has a beneficial role in reducing oxidative stress and atherogenesis, but human studies have shown that Lp-PLA$_2$ is a modest independent predictive biomarker of CVD. Interestingly, the enzyme Lp-PLA$_2$ is mostly associated with LDL, but when assayed at equimolar protein concentrations, Lp(a) contains 1.5-2 fold higher mass and several-fold greater Lp-PLA$_2$ activity compared with LDL, even though Lp-PLA$_2$ is associated with the apoB but not the apo(a) moiety of Lp(a). Furthermore, smaller apo(a) isoforms exhibit higher apparent Lp-PLA$_2$ $K_m$ and $V_{max}$ values, compared to large ones, suggesting that the apo(a) may influence the association of Lp-PLA$_2$ with Lp(a). Under normal physiological conditions Lp(a) may function in binding and facilitating degradation of OxPL since it is enriched in Lp-PLA$_2$. This would be consistent with the observation that at low levels Lp(a) may have a beneficial effect, as evidenced by the J-shaped curve (FIG. 6). However, in patients with elevated Lp(a) levels, this potential physiological function may be overwhelmed. In support of this concept, it was shown that, compared to those without CAD, patients with CAD have significantly lower Lp-PLA$_2$ mass and activity on isolated Lp(a) particles, but normal LDL-associated Lp-PLA$_2$ mass and activity is present in both patients with and without CAD. Interestingly, removal of apo(a) from the Lp(a) particle, resulted in a significant increase in the Lp-PLA$_2$ activity.

The disclosure demonstrates that OxPL/apoB levels independently predict 10-year cardiovascular events in an unselected population, and in a manner strikingly similar to Lp(a), and suggests that the atherogenicity of Lp(a) may be derived in part from its association with OxPL. The synergistic association between OxPL/apoB, Lp(a) and Lp-PLA$_2$ activity on CVD risk suggests that these particles may be pathophysiologically linked in the normal metabolism of OxPL and in mediating atherogenesis.

The disclosure demonstrates that subjects in the highest quartile of OxPL/apoB have significantly higher risk of future CHD events compared to those in the lowest quartile. Furthermore, the risk of future CHD events was significantly potentiated by elevated activity levels of sPLA$_2$ and Lp-PLA$_2$. Subjects in the highest tertiles of both OxPL/apoB and Lp-PLA$_2$ or OxPL/apoB and sPLA$_2$ or OxPL/apoB and sPLA$_2$ and Lp-PLA$_2$ had significantly higher risk of future CHD than subjects in the lowest tertiles.

Thus, the disclosure provides methods and compositions useful for predicting cardiovascular disease risk in a subject. The method includes measuring the OxPL/apoB ratio and further measuring the activity of Lp-PLA$_2$ and/or sPLA$_2$ in a subject. Elevated OxPL/apoB levels are a strong, independent predictor of CHD events. The predictive values is further enhanced by elevated activity levels of sPLA2 and Lp-PLA2, which mediate breakdown of OxPL present on lipoproteins and within atherosclerotic lesions. This study links several pathophysiologically related oxidative biomarkers in the prediction of CHD events and suggests novel approaches to predicting CHD risk.

In one embodiment, of the disclosure a method for determining a subject's predisposition to coronary artery disease is provided. The method includes determining a subject's plasma OxPL level; determining the subject's Lp-PLA$_2$ or sPLA$_2$ mass or activity; and correlating the OxPL level with the Lp-PLA$_2$ or sPLA$_2$ level, wherein increased levels of OxPL and Lp-PLA$_2$ and/or sPLA$_2$ are indicative of a predisposition to coronary artery disease. The amount of OxPL can be detected using an antibody that specifically binds to an OxPL such as, but not limited to, a monoclonal antibody. Exemplary monoclonal antibodies include E06 or DLH3. In another embodiment, the antibody binds an ApoB epitope. In another embodiment, an antibody that binds an OxPL or ApoB may be immobilized on a substrate array. Typically the subject is human although the methods may be used in veterinary procedures. In one embodiment, the OxPL is associated with apolipoprotein B-100 (apoB) particles In another embodiment, the OxPL is associated with lipoprotein (a) (Lp(a)).

The method can be carried out on a biological sample obtained from a subject. The biological sample can be, for example, blood, serum, or plasma.

Methods for measuring the ratio of OxPL/apoB are described in U.S. Patent Publication No. 20060177435, the disclosure of which is incorporated herein by reference. The methods are based on the determination of OxPL levels in the sample, the determination of apoB levels in the sample and then determining the ratio of OxPL to apoB (OxPL/apoB).

In one embodiment, the level of OxPL and the level of apoB in the sample are measured with two or more different biomolecules. For example a first biomolecule that specifically interact with OxPL and the second biomolecules the specifically interacts with apoB can be used. In some embodiments the biomolecules are antibodies, such as, for example monoclonal antibodies that interact with OxPL (e.g., E06 or DLH3 antibodies). In other aspects, the biomolecules are antigens that can be used to recognize the presence of antibodies to OxPL or apoB. In some embodiments, the biomolecules are immobilized to form an array comprising a first set of a plurality of the first biomolecule and a second set of a plurality of the second biomolecule.

Exemplary oxidized phospholipids include oxidized forms of 1-palmitoyl-2-arachidonoyl-sn-glycero-3phosphorylcholine (Ox-PAPC), 1-palmitoyl-2-oxovaleroyl-sn-glycero-3-phosphoryl-choline (POVPC), 1-palmitoyl-glutaroyl-sn-glycero-3-phosphorylcholine (PGPC), 1-palmitoyl-2-epoxyisoprostane-sn-glycero-3-phosphorylcholine (Ox-SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine (SEIPE).

An exemplary biochemical test for identifying specific proteins, such as OxPL and apoB, employs a standardized test format, such as the Enzyme Linked Immunosorbent Assay or ELISA test, although the information provided herein may apply to the development of other biochemical or diagnostic tests and is not limited to the development of an ELISA test. Various commercially available ELISA kits are available.

In one embodiment, an immunoassay can be performed either by first capturing the LDL on a microtiter well by use of an antibody that binds to both oxidized and non-oxidized LDL (e.g., an anti-apoB), and then detection of the OxLDL by a labeled E06 antibody. Alternatively, E06 antibody can be bound to the bottom of the microtiter well and the amount of OxLDL bound determined by the use of a labeled anti-LDL antibody. OxLDL could also be used to coat the microtiter wells and various concentration of patient sera, putatively containing OxLDL, could be mixed with a constant, limiting amount of labeled (e.g., biotinylated) E06 to compete for binding to the OxLDL on the plate. For each assay, under standard conditions, a standard curve could be developed using PC as a competing agent rather than patient sera.

Lp-PLA$_2$ mass and activity can be determined in a number of ways. For example, a sample of blood is taken from a patient, the plasma/serum sample prepared and passed through a dextran sulphate column pre-equilibrated with 0.9% (w/v) NaCl solution. Following washes with the same salt solution Lp-PLA$_2$ is eluted with a 4.1% (w/v) NaCl solution. Heparin agarose columns can also be used with the wash and elution solutions containing 0.7% and 2.9% NaCl, respectively.

Enzymatic activity can be measured by monitoring the absorbance change at 400 nm. Purified enzyme is pre-incubated at 37° C. and substrate is added after 5 minutes. The absorbance change at 400 nm is monitored for 20 minutes. In addition, antibodies have also been developed that bind to Lp-PLA$_2$.

The ratios and activity factors above may be further combined with additional genetic factor measurements. For example, genetic variations in the interleukin-1 (IL-1) region are associated with increased inflammatory mediators and early cardiovascular events. The disclosure demonstrates that IL-1 genetic differences that are known to be associated with inflammatory responsiveness strongly influence the risk of CAD mediated by OxPL/apoB and Lp(a). Patients with pro-inflammatory IL-1(+) genotypes were at a continuum of risk for the presence of CAD, defined as >50% diameter stenosis, whereas patients with IL-1(−) genotypes seemed to be insensitive to risk for CAD mediated by increasing OxPL/apoB or Lp(a) levels. These findings were independent of CRP levels indicating that this influence on CAD is a more proximal effect on the inflammatory cascade. This provides evidence of a biological link between genetic predisposition to inflammation, lipid disorders, oxidation of lipoproteins and clinically manifest CAD and highlights the effect of specific genetic factors in accelerating or attenuating atherogenesis. Accordingly, measurement of IL-1 provides, in combination with OxPL/ApoB and Lp-PLA2 mass or activity, provides further predictive power.

The IL-1 gene cluster is on the long arm of chromosome 2 (2q13) and contains at least the genes for IL-1 alpha (IL-1A), IL-1 beta (IL-1B), and the IL-1 receptor antagonist (IL-1RN), within a region of 430 Kb (Nicklin, et al. (1994) Genomics, 19: 382-4). The agonist molecules, IL-1 alpha and IL-1 beta, have potent pro-inflammatory activity and are at the head of many inflammatory cascades. Their actions, often via the induction of other cytokines such as IL-6 and IL-8, lead to activation and recruitment of leukocytes into damaged tissue, local production of vasoactive agents, fever response in the brain and hepatic acute phase response. All three IL-1 molecules bind to type I and to type II IL-1 receptors, but only the type I receptor transduces a signal to the interior of the cell. In contrast, the type II receptor is shed from the cell membrane and acts as a decoy receptor. The receptor antagonist and the type II receptor, therefore, are both anti-inflammatory in their actions.

Certain alleles from the IL-1 gene cluster are known to be associated with particular disease states. For example, IL-1RN (VNTR) allele 2 has been shown to be associated with osteoporosis (U.S. Pat. No. 5,698,399), nephropathy in diabetes mellitus (Blakemore, et al. (1996) Hum. Genet. 97(3): 369-74), alopecia greata (Cork, et al., (1995) J. Invest. Dermatol. 104(5 Supp.): 15S-16S; Cork et al. (1996) Dermatol Clin 14: 671-8), Graves disease (Blakemore, et al. (1995) J. Clin. Endocrinol. 80(1): 111-5), systemic lupus erythematosus (Blakemore, et al. (1994) Arthritis Rheum. 37: 1380-85), lichen sclerosis (Clay, et al. (1994) Hum. Genet. 94: 407-10), and ulcerative colitis (Mansfield, et al. (1994) Gastoenterol. 106(3): 637-42)).

In addition, the IL-1A allele 2 from marker −889 and IL-1B (TaqI) allele 2 from marker +3954 have been found to be associated with periodontal disease (U.S. Pat. No. 5,686,246; Kornman and diGiovine (1998) Ann Periodont 3: 327-38; Hart and Kornman (1997) Periodontol 2000 14: 202-15; Newman (1997) Compend Contin Educ Dent 18: 881-4; Kornman et al. (1997) J. Clin Periodontol 24: 72-77). The IL-1A allele 2 from marker −889 has also been found to be associated with juvenile chronic arthritis, particularly chronic iridocyclitis (McDowell, et al. (1995) Arthritis Rheum. 38: 221-28). The IL-1B (TaqI) allele 2 from marker +3954 of IL-1B has also been found to be associated with psoriasis and insulin dependent diabetes in DR3/4 patients (di Giovine, et al. (1995) Cytokine 7: 606; Pociot, et al. (1992) Eur J. Clin. Invest. 22: 396-402). Additionally, the IL-1RN (VNTR) allele 1 has been found to be associated with diabetic retinopathy (see U.S. Ser. No. 09/037,472, and PCT/GB97/02790). Furthermore allele 2 of IL-1 RN (VNTR) has been found to be associated with ulcerative colitis in Caucasian populations from North America and Europe (Mansfield, J. et al., (1994) Gastroenterology 106: 637-42). Interestingly, this association is particularly strong within populations of ethnically related Ashkenazi Jews (PCT WO97/25445).

Traditional methods for the screening of heritable diseases have depended on either the identification of abnormal gene products (e.g., sickle cell anemia) or an abnormal phenotype (e.g., mental retardation). These methods are of limited utility for heritable diseases with late onset and no easily identifiable phenotypes such as, for example, vascular disease. With the development of simple and inexpensive genetic screening methodology, it is now possible to identify polymorphisms that indicate a propensity to develop disease, even when the disease is of polygenic origin. The number of diseases that can be screened by molecular biological methods continues to grow with increased understanding of the genetic basis of multifactorial disorders.

Many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic-occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in an individual. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

The term "haplotypes" as used herein refers to groupings of two or more SNPs that are physically present on the same chromosome which tend to be inherited together except when recombination occurs. The haplotype provides information regarding an allele of the gene, regulatory regions or other genetic sequences affecting a trait. The linkage disequilibrium and, thus, association of a SNP or a haplotype allele(s) and a trait can be strong enough to be detected using simple genetic approaches, or can require more sophisticated statistical approaches to be identified.

Since genomic DNA is double-stranded, each SNP can be defined in terms of either the plus strand or the minus strand. Thus, for every SNP, one strand will contain an immediately 5'-proximal invariant sequence and the other strand will contain an immediately 3'-distal invariant sequence.

Polymorphisms are allelic variants that occur in a population that can be a single nucleotide difference present at a locus, or can be an insertion or deletion of one, a few or many consecutive nucleotides. As such, a single nucleotide polymorphism (SNP) is characterized by the presence in a population of one or two, three or four nucleotides (i.e., adenosine, cytosine, guanosine or thymidine), typically less than all four nucleotides, at a particular locus in a genome such as the human genome. SNPs are positions at which two alternative bases occur at appreciable frequency (>1%) in a given population, and are the most common type of genetic variation. The site is usually preceded by and followed by highly conserved sequences of the allele (e.g., sequences that vary in less than $\frac{1}{100}$ or $\frac{1}{1000}$ members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Single nucleotide polymorphisms may be functional or non-functional. Functional polymorphisms affect gene regulation or protein sequence whereas non-functional polymorphisms do not. Depending on the site of the polymorphism and importance of the change, functional polymorphisms can also cause, or contribute to diseases.

SNPs can occur at different locations of the gene and may affect its function. For instance, polymorphisms in promoter and enhancer regions can affect gene function by modulating transcription, particularly if they are situated at recognition sites for DNA binding proteins. Polymorphisms in the 5' untranslated region of genes can affect the efficiency with which proteins are translated. Polymorphisms in the protein-coding region of genes can alter the amino acid sequence and thereby alter gene function. Polymorphisms in the 3' untranslated region of gene can affect gene function by altering the secondary structure of RNA and efficiency of translation or by affecting motifs in the RNA that bind proteins which regulate RNA degradation. Polymorphisms within introns can affect gene function by affecting RNA splicing.

Medium to high-throughput systems for analyzing SNPs, known in the art such as the SNPStream®. UHT Genotyping System (Beckman/Coulter, Fullerton, Calif.) (Boyce-Jacino and Goelet patents), the Mass Array™ system (Sequenom, San Diego, Calif.) (Storm, N. et al., Methods in Molecular Biology. 212: 241-262, 2002), the BeadArray™ SNP genotyping system available from Illumina (San Diego, Calif.) (Oliphant, A., et al. (June 2002) (supplement to Biotechniques), and TaqMan™ (Applied Biosystems, Foster City, Calif.) can be used with the present invention. The system can be a microfluidic device. Numerous microfluidic devices are known that include solid supports with microchannels (See e.g., U.S. Pat. Nos. 5,304,487, 5,110,745, 5,681,484, and 5,593,838).

Genetic screening (also called genotyping or molecular screening), can be broadly defined as testing to determine if a patient has mutations (or alleles or polymorphisms) that either cause a disease state or are "linked" to the mutation causing a disease state. Linkage refers to the phenomenon wherein DNA sequences which are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in linkage disequilibrium with one another because, in a given human population, they tend to either both occur together or else not occur at all in any particular member of the population. Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

While the frequency of meiotic recombination between two markers is generally proportional to the physical distance between them on the chromosome, the occurrence of "hot spots" as well as regions of repressed chromosomal recombination can result in discrepancies between the physical and recombinational distance between two markers. Thus, in certain chromosomal regions, multiple polymorphic loci spanning a broad chromosomal domain may be in linkage disequilibrium with one another, and thereby define a broad-spanning genetic haplotype. Furthermore, where a disease-causing mutation is found within or in linkage with this haplotype, one or more polymorphic alleles of the haplotype can be used as a diagnostic or prognostic indicator of the likelihood of developing the disease. This association between otherwise benign polymorphisms and a disease-causing polymorphism occurs if the disease mutation arose in the recent past, so that sufficient time has not elapsed for equilibrium to be achieved through recombination events. Therefore identification of a human haplotype which spans or is linked to a disease-causing mutational change, serves as a predictive measure of an individual's likelihood of having inherited that disease-causing mutation. Importantly, such prognostic or diagnostic procedures can be utilized without necessitating the identification and isolation of the actual disease-causing lesion. This is significant because the precise determination of the molecular defect involved in a disease process can be difficult and laborious, especially in the case of multifactorial diseases such as inflammatory disorders.

The term "allele" refers to the different sequence variants found at different polymorphic regions. The sequence variants may be single or multiple base changes, including without limitation insertions, deletions, or substitutions, or may be a variable number of sequence repeats.

The term "allelic pattern" refers to the identity of an allele or alleles at one or more polymorphic regions. Alternatively, an allelic pattern may consist of either a homozygous or heterozygous state at a single polymorphic site. Alternatively, an allelic pattern may consist of the identity of alleles at more than one polymorphic site.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested. For example, the controls may be a sample of genomic DNA or a cloned portion of the IL-1 gene cluster. However, where the sample to be tested is genomic DNA, the control sample is preferably a highly purified or isolated sample of genomic DNA.

The terms "IL-1 gene cluster" and "IL-1 loci" as used herein include all the nucleic acid at or near the 2q13 region of chromosome 2, including at least the IL-1A, IL-1B and IL-1RN genes and any other linked sequences. (Nicklin et al., Genomics 19: 382-84, 1994). The terms "IL-1A", "IL-1B", and "IL-1RN" as used herein refer to the genes coding for IL-1 alpha, IL-1 beta, and IL-1 receptor antagonist, respectively. The gene accession number for IL-1A, IL-1B, and IL-1RN are X03833, X04500, and X64532, respectively.

"IL-1 functional mutation" refers to a mutation within the IL-1 gene cluster that results in an altered phenotype (i.e. affects the function of an IL-1 gene or protein).

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject IL-1 polypeptides preferably includes no more than 10 kilobases (kb) of nucleic acid sequence which naturally immediately flanks the IL-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The measurements obtained for Lp-PLA$_2$ activity and OxPL/apoB and optionally other cardiovascular risk factors (e.g., IL-1 polymorphisms, or sPLA$_2$ activity) are combined in a statistical sanalysis, wherein the combined value of LP-PLA$_2$ activity and OxPL/apoB and optionally other risk factors are indicative of having or a risk of having or developing a cardiovascular disease and/or cardiovascular event.

Risk factor measurements may be combined by any appropriate state of the art mathematical methods. Well-known mathematical methods for correlating a marker combination to a disease employ methods such as, but not limited to, Discriminant analysis (i.e., linear-, quadratic-, regularized-discriminate analysis), Kernal Methods (e.g., SVM), non-paramaetric methods (e.g., k-nearest-neighbor classifiers), PLS (Partial Least squares), Tree-based methods (e.g., logic regression, CART, Random Forest methods, Boosting/Bagging methods), Generalized Linear models (e.g., logistic regression), principal components based methods (e.g., SIMICA), Generalized additive meodels, Fuzzy Logic based methods, neural networks and genetic algorithm based methods. The skilled artisan will have no problem in selecting an appropriate method to evaluate a marker combination as well as threshold values. Details relating to these statistical methods are found in the following references: Ruczinski et al. J. of Computational and Graphical Statistics, 12:475-511, 2003; Friedman, J. H., J. of the Amer. Statistical Assoc., 84:165-175, 1989; Hastie et al., The elements of statistical Learning, Springer Verlag, 2001; Breiman et al., Classification and regression trees, California: Wadsworth; Breiman et al. Machine Learning, 45:5-32, 2001; Pepe M. S., The Statistical Evaluation of Medical Tests for Classification and Prediction, Oxford Statistical Science Series, 28 (2003); and Duda et al., Pattern Classification, Wiley Interscience, $2^{nd}$ Edition, 2001; the disclosures of which are incorporated herein by reference.

In one embodiment, an optimized multivariate cut-off for the underlying combination of risk factors is used to discriminate state A from state B, e.g., diseased from substantially healthy. In this type of analysis, the risk factors are no longer independent but form a risk factor panel. Combining the measurements of Lp-PLA2 activity and OxPL/apoB significantly improves the diagnostic/prognostic accuracy for cardiovascular disease and/or cardiovascular event as compared to substantially healthy subjects of as compared to subject which have been diagnosed for a cardiovascular disease or event.

In another embodiment, the statistical analysis of the measurements of Lp-PLA2 and OxPL/apoB and optionally other cardiovascular risk factors (e.g., IL-1 markers and/or sPLA2 activity) is based on the determination of odds ratios (OR) using standard procedures. An odds ratio is calculated by dividing the odds in the test group by the odds in the control group. The odds of an event are calculated as the number of events divided by the number of non-events. If the odds of an event are greater than one, the event is more likely to happen than not (the odds of an event that is certain to happen are infinite); if the odds are less than one the chances are that the event will not happen (the odds of an impossible event are zero). In general, the strength of association is reported as odds ratios (OR) (with 95% lower (LCL) and upper (UCL) confidence limit), indicating the factor by which the risk of having a disease or being at risk of having or developing a disease is increased (OR>1). The 95% confidence interval (95% CI) is the range of numerical values used to be confidence (to a computed probability of 95%) that the population value being estimated will be found. Confidence intervals indicate the strength of evidence; where confidence intervals are wide, they indicate less precise estimates of effect. The larger the trial's sample size, the larger the number of outcome evens and the greater becomes the confidence that the true relative risk reduction is close to the value state. Thus the confidence intervals get narrower and prediction is increased. To confidently accept a calculated OR as reliable, important or clinically significant, the lower boundary of the confidence interval, or lower confidence limit, should be >1 if the OR>1, or the upper boundary of the confidence interval should be <1 if the OR<1.

In one embodiment of the disclosure, the combined value of Lp-PLA$_2$ activity and OxPL/apoB and optionally other risk factors is compared to a reference value. In one embodiment the reference value may be an index value or may be derived from one or more risk prediction algorithms or computed indices for the cardiovascular disease and/or cardiovascular event. A reference value can be relative to a number or value derived from population studies including without limitation, such subject having similar body mass index, total cholesterol levels, LDL/HDL levels, systolic or diastolic blood pressure, similar age range, subject in the same of similar ethnic group, subject with family histories or atherosclerosis, atherothrombosis, or CAD, PAD or DVD, or relative to the starting sample of a subject undergoing treatment for an arteriovascular disease, such as atherosclerosis, atherothrombosis, CAD, PAD or DVD. Such reference values can be derived from statistical analysis and/or risk prediction data of populations obtained from mathematical algorithms and computed indices or arteriovascular disease, such as, but not limited to, algorithms reported in the Framingham Study.

In one embodiment, the reference value is derived from the combination of OxPL/apoB and Lp-PLA$_2$ activity and optionally other factors in a control sample derived from one or more subjects which are substantially healthy. Such subject who are substantially healthy lack traditional risk factors for cardiovascular disease: for example, those subject have a serum cholesterol level less than 200 mg/dl, systolic blood pressure less than or equal to 120 mm Hg, diastolic blood pressure less than or equal to 80 mm Hg, non-current smoker, no history of diagnosed diabetes, no previously diagnosed acute coronary syndrome or hypertension, no family history of cardiovascular disease or disorders. The foregoing factors can be assessed through routine testing either invasive or non-invasive diagnostics including, but not limited to, electrocardiograms, carotid B-mode ultrasound, electron beam computed tomography, coronary calcium scoring, multi-slice high resolution computer tomography, nuclear magnetic resonance stress exercise testing, angiography, intra-vascular ultrasound, and the like.

In another embodiment, such subject are monitored and/or periodically retested for a diagnostically relevant period of time ("longitudinal studies") following such test to verify continued absence from cardiovascular disease or acute cardiovascular events (disease or event free survival). Such period of time may be one year, two years, two to five years, five years, five to ten ears, ten years, or ten or more years form the initial testing date for determination of the reference value. Furthermore, retrospective measurement of OxPL/apoB and Lp-PLA$_2$ activity levels can be performed in properly banked samples.

The term "treating" as used herein is intended to encompass curing as well as ameliorating at least one symptom of a disease or at least one abnormality associated with a disorder. Treating a cardiovascular disorder can take place by administering a cardiovascular disorder therapeutic. Treating a cardiovascular disorder can also take place by modifying risk factors that are related to the cardiovascular disorder.

A "treatment plan" refers to at least one intervention undertaken to modify the effect of a risk factor upon a patient. A treatment plan for a cardiovascular disorder or disease can address those risk factors that pertain to cardiovascular disorders or diseases. A treatment plan can include an intervention that focuses on changing patient behavior, such as stopping smoking. A treatment plan can include an intervention whereby a therapeutic agent is administered to a patient. As examples, cholesterol levels can be lowered with proper medication, and diabetes can be controlled with insulin. Nicotine addiction can be treated by withdrawal medications. A treatment plan can include an intervention that is diagnostic. The presence of the risk factor of hypertension, for example, can give rise to a diagnostic intervention whereby the etiology of the hypertension is determined. After the reason for the hypertension is identified, further treatments may be administered.

EXAMPLES

The invention is illustrated in the following examples, which are provided by way of illustration and are not intended to be limiting.

Example 1

OxPL/apoB and Lp(a) levels were measured in 504 patients undergoing coronary angiography. Coronary artery disease (CAD) was defined as >50% diameter stenosis. Three single nucleotide polymorphisms (SNPs) in the IL-1 gene cluster associated with enhanced pro-inflammatory responses, IL-1A(+4845) (G/T), IL-1B(+3954) (C/T), and IL-1B(−511) (C/T), were used to create a composite genotype termed IL-1(+). All other genotypes not associated with higher levels of pro-inflammatory cytokines were termed IL1(−).

Among IL-1(+) patients, those in the highest quartile of OxPL/apoB had a significantly higher risk of CAD compared with those in the lowest quartile (OR 2.52, P<0.01). This effect was strongly accentuated in patients ≦60 years old (OR 6.92, P=0.0001). In contrast, in IL-1(−) patients, OxPL/apoB levels showed no association with CAD in any group. Substituting Lp(a) for OxPL/apoB gave similar results for both genotype groups, except in patients ≦60 years old where OxPL/apoB was predictive of CAD even with Lp(a) in the model. These findings were independent of all other measured risk factors, including C-reactive protein.

The influence of OxPL and Lp(a) on CAD is conditional upon IL-1 genotype status. These data suggest a novel and clinically relevant biological link between pro-inflammatory IL-1 genotypes, oxidation of phospholipids and genetic predisposition to CAD in younger individuals.

Study design: 504 eligible, consecutive patients (>97% Caucasian), age 18 to 75, undergoing clinically indicated coronary angiography were recruited from June-December 1998. The study was prospectively designed to test the association of CAD with specific IL-1 genotype groups that were associated with higher inflammatory responses. Patients with prior coronary revascularization and diabetes mellitus were excluded to avoid potential enrichment with cases that may have confounding etiological factors.

Angiographic analysis: CAD was defined as >50% diameter stenosis in one or more of the 3 major coronary arteries.

Determination of OxPL/apoB Levels: The content of OxPL per apoB-100 particle (OxPL/apoB) was measured by chemiluminescent ELISA using the murine monoclonal antibody E06, which binds to the phosphorylcholine (PC) headgroup of oxidized but not native phospholipids. Equal numbers of apoB-100 particles are captured from each plasma sample and thus the content of OxPL is normalized for apoB-100 in each subject. Thus, by design, the OxPL/apoB measurement is independent of apoB-100 (and LDL-cholesterol) levels.

Laboratory analyses: Apolipoprotein B-100, Lp(a), total cholesterol, HDL cholesterol (HDL-C) and triglycerides were measured with commercially available kits. LDL cholesterol (LDL-C) was estimated from the Friedewald formula. High sensitivity CRP (lower range 0.15 mg/L) was measured.

Genetic analyses: DNA was extracted and genotyping was performed at the Division of Genomic Medicine, University of Sheffield, UK. All genetic analyses were performed blinded to clinical data. Genotyping was performed by a 5' nuclease assay (Taqman™; Hoffman-LaRoche, Inc.) based on the 5' nuclease activity of Taq Polymerase and the detection by FRET of the cleavage of two probes, designed to match and hybridize to either allele copy during PCR. Single nucleotide polymorphisms (SNPs) were genotyped at two loci in the gene for IL-1 beta [IL1B(−511) and IL1B(+3954)], and at one locus in the gene for IL-1 alpha [IL1A(+4845)]. At locus IL1B(−511), cytosine (C) is the more common nucleotide base and thymine (T) is the less common base, a C to T transition. The SNP at IL1B(+3954) is also a C to T transition, and the SNP at IL1A(+4845) is a G to T transition. Given two copies of each chromosome, the genotype at each locus will consist of two bases, which may be in three configurations—e.g. an individual's genotype at IL1B(−511) may be homozygous for the C allele (C/C), heterozygous (C/T), or homozygous for the T allele (T/T).

Approximately 20% of the samples were evaluated as duplicates, which were blinded to laboratory personnel to test reproducibility of the genotyping methods. There was 100% concordance between all duplicate samples.

IL-1 composite genotype patterns used for association with biochemical and clinical parameters: the study was designed to evaluate the relationship between CAD and IL-1 genotypes that are associated with differential expression of inflammatory mediators. The three IL-1 SNPs were selected based on the following: a) IL1B(−511) allele C has been associated with increased expression of IL-1 beta protein and with increased risk for cardiovascular events; 7 and b) IL1B(+3954) allele T, either alone or in combination with IL1A(+4845) allele T, has been associated with increased levels of IL-1 and CRP. Two groups of genotypes were defined, the first group, IL1(+), includes composite genotypes with IL1 alleles that have been previously associated with over-expression of inflammatory mediators; and the second group, IL1(−), includes all other genotypes which have not been associated with over-expression of inflammatory mediators.

A small number of highly prevalent haplotypes have been described for the IL1 gene cluster. True haplotypes, as defined by a linkage disequilibrium block on a single chromosome, can be definitively ascertained in haploid entities such as a single sperm, but genotyping of alleles in a cell with paired chromosomes does not, per se, assign a mutation to a specific chromosome within a chromosome pair. Thus putative haplotypes were assigned based on mathematical probability applied to the genotypes ascertained in a diploid cell. The three SNPs used in this study tag five predominant IL1 haplotypes that account for 93.5% of observed haplotypes in this Caucasian population, with three haplotypes accounting for 83.6% of the haplotypes. The three dominant haplotypes comprised of IL1A(+4845), IL1B(+3954), and IL1B(−511) are: 1) GCC (frequency 39.8%), 2) GCT (25.7%), and 3) TTC (18.1%). Haplotype #3 (TTC) includes, at each of the three loci, the allele associated with over-expression of inflammatory mediators. Included in the IL1(+) group are all composite genotypes that include at least one copy of haplotype #3. In addition, because IL1B(−511) genotype C/C has been associated with the highest production of IL-1 beta protein and with the greatest risk for early MI, the IL1(+) group also includes all composite genotypes with IL1B(−511) genotype C/C that are composed of haplotypes other than haplotype #3. The IL-1 genotypes that result from the predominant haplotypes in this Caucasian population are shown below in Table A, and the genotypes comprising the IL1(+) and IL1(−) groups are indicated.

TABLE A

|       | GCC[1]         | GCT             | TTC                  | TCC                    | TCT                    |
|-------|----------------|-----------------|----------------------|------------------------|------------------------|
| GCC   | GG/CC/CC[2,4]  | GG/CC/CT[5]     | CT/CT/CC[3,4]        | GT/CC/CC[4]            | GT/CC/CT[5]            |
| GCT   |                | GG/CC/TT[5]     | GT/CT/CT[3]          | GT/CC/CT[5]            | GT/CC/TT[5]            |
| TTC   |                |                 | TT/TT/CC[3,4]        | TT/CT/CC[3,4]          | TT/CT/CT[3]            |
| TCC   |                |                 |                      | TT/CC/CC[4]            | TT/CC/CT[5]            |
| TCT   |                |                 |                      |                        | TT/CC/TT[5]            |

[1] The nucleotides comprising a specific haplotype at the genetic loci IL1A(+4845), IL1B(+3954), and IL1B (-511).
[2] The composite genotype resulting from combination of the two haplotypes that intersect at this cell. The genotypes are presented in the order IL1A(+4845)/IL1B(+3954)/IL1B(-511).
[3] The genotype includes at least one copy of haplotype TTC and is included in the IL(+) group.
[4] The genotype includes two copies of allele C at IL1B(−511), which has been associated with the highest production of IL-1 beta protein and with greatest risk for early MI.[7] This genotype is included in the IL1(+) group.
[5] The genotype is included in the IL1(−) group.

Figure 2:
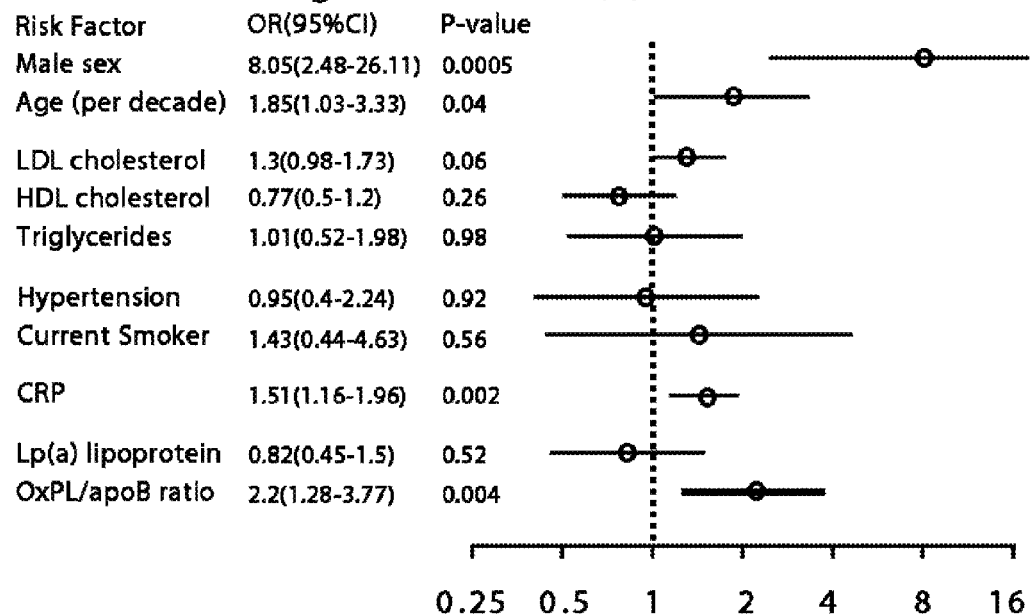
FIG. 2, panels A-D depict odds ratios for CAD associated with selected risk factors among patients $\leq 60$ years old and $>60$ years old stratified by genotype. CI=confidence interval, LDL=low-density lipoprotein (per increase of 25 mg/dl), CRP=C-reactive protein (per doubling), OxPL/apoB ratio is the ratio of oxidized phospholipid content per apolipoprotein B-100 (per doubling), HDL=high-density lipoprotein (per increase of 10 mg/dl), and triglycerides (per doubling). Age is measured per decade. Current smoking was deleted as a factor for those $>60$ years old because of negligible sample size of smokers in this category.
Figure 2:
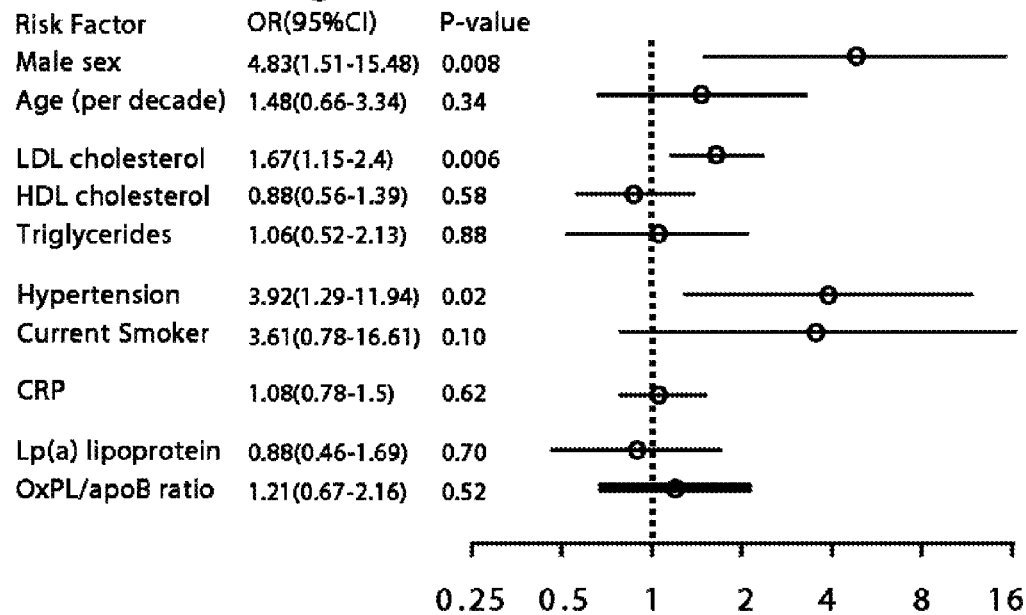
Figure 2:
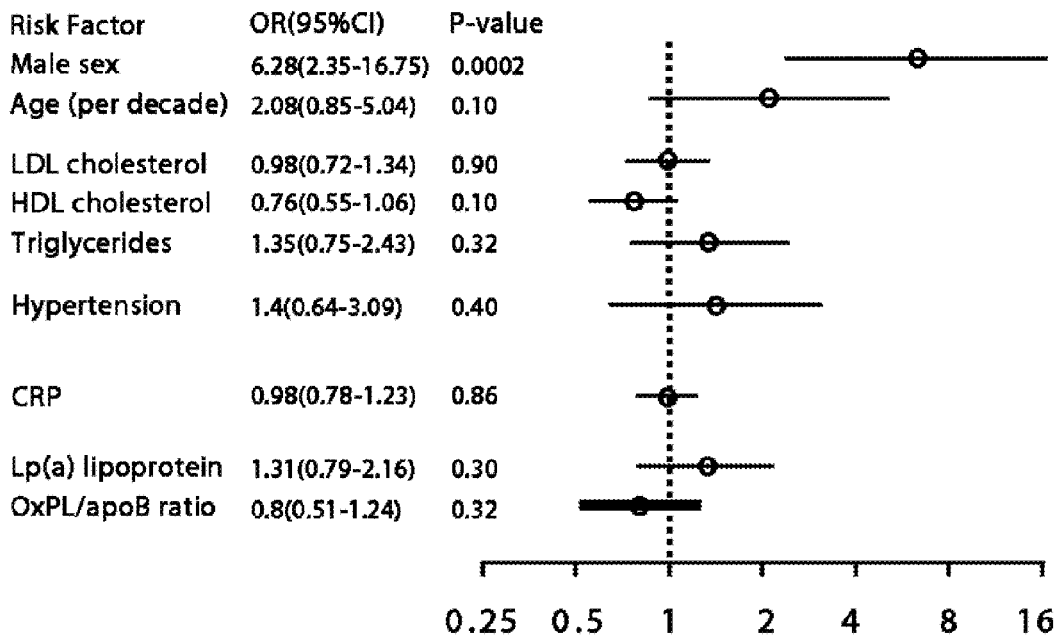
Figure 2:
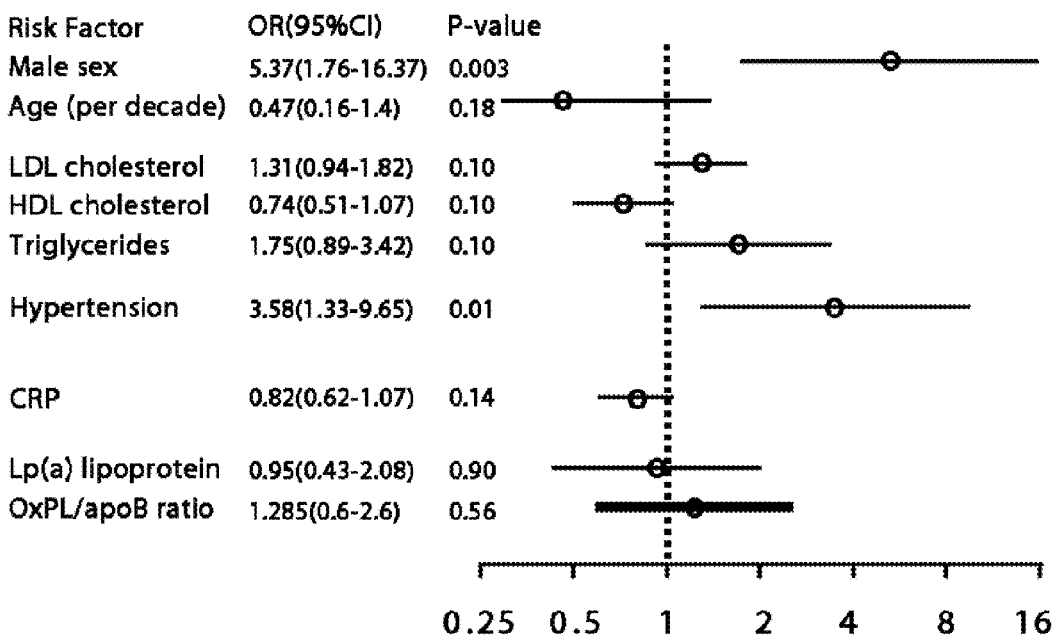

Statistical Analysis: Discrete data are presented as frequencies and percentages, and continuous variables as means and standard deviations or as medians and interquartile ranges if the distributions were skewed. The percentage of patients with CAD and the odds ratios (OR) was calculated for quartiles of the OxPL/apoB ratio and Lp(a). Since the association between OxPL/apoB levels and CAD was shown to be stronger in patients ≦60 years, analyses were performed for all patients, according to age (≦60 years or >60 years), and according to IL-1 genotype status. Logistic-regression models were used to quantify further the relationships between OxPL/apoB and Lp(a) levels and CAD (Tables 2 and 3). To evaluate the effect of IL-1 genotype on the associations between the OxPL/apoB ratio or Lp(a) and CAD, patients were stratified by genotype and OR were plotted for differences between any two OxPL/apoB ratios or Lp(a) within the interquartile range (FIG. 1). Age at presentation to the cardiac catheterization laboratory by IL-1 genotype was evaluated by linear regression. Multiple logistic-regression analysis was used to estimate the partial associations between the OxPL/apoB and Lp(a) levels and CAD, with adjustment for age, sex, smoking status, the presence or absence of hypertension, LDL cholesterol, HDL cholesterol, triglycerides, and CRP levels (FIG. 2). This analysis was further stratified into patients above and below the median CRP levels of 3.0 mg/L to assess whether the IL-1 genotype influence was attributable to CRP. The base-2 logarithms ($\log_2$) of OxPL/apoB, Lp(a), triglycerides and CRP were used in all the logistic regression models to account for skewness in the distributions. Thus, odds ratios for these variables reflect the change in odds for an increase of 1 $\log_2$ (the equivalent of a doubling of the value) in the measure.

Baseline Characteristics of the Study Group: Table 1 displays the baseline characteristics of the entire study group and of the IL-1(+) and IL-1(−) groups. IL-1(+) patients represented 60% of the population. There were no significant differences in any parameters between IL-1(+) and IL-1(−) patients, except a trend of previous myocardial infarction (18% vs. 12%, P=0.08) and a slightly higher frequency of white race in the IL-1(+) group (99% vs. 96%, P=0.03).

TABLE 1

Baseline characteristics and lipid levels in the study Group.

| Variable | All | IL-1 positive | IL-1 negative | p-Value IL-1 effect |
|---|---|---|---|---|
| Number | 504 | 300[1] | 201 | — |
| Age-yr | 60.1 ± 10.9[2] | 59.6 ± 11.1 | 60.6 ± 10.7 | 0.32 |
| Female sex-no. (%) | 193 (38) | 11 (37) | 80 (40) | 0.53 |
| White race-no. (%) | 490 (97) | 295 (99) | 192 (96) | 0.03 |
| Hypertension-no. (%) | 232 (46) | 141 (47) | 91 (45) | 0.70 |
| Current smoker-no. (%) | 40 (8) | 24 (8) | 16 (8) | 0.99 |
| Previous myocardial infarction-no. (%) | 77 (15) | 53 (18) | 24 (12) | 0.08 |
| Congestive Heart failure-no. (%) | 59 (12) | 32 (11) | 27 (13) | 0.35 |
| Family history of CAD-no. (%) | 128 (25) | 76 (25) | 50 (25) | 0.91 |
| Lipid levels-mg/dl | | | | |
| Total cholesterol | 207 ± 45 | 208 ± 46 | 206 ± 43 | 0.56 |
| LDL cholesterol | 124 ± 37 | 124 ± 35 | 125 ± 40 | 0.81 |
| HDL cholesterol | 48 ± 15 | 48 ± 15 | 48 ± 14 | 0.99 |
| Triglycerides | | | | |
| Median | 153 | 155 | 151 | 0.29 |
| Interquartile range | 112-207 | 113-220 | 107-198 | |
| Apolipoprotein B-100 | 98 ± 21 | 98 ± 20 | 98 ± 20 | 0.93 |
| Lp(a) lipoprotein | | | | |
| Median | 21.1 | 21.5 | 20.0 | 0.72 |
| Interquartile range | 8.8-39.6 | 9.2-38.0 | 7.8-41.6 | |
| C-reactive protein-mg/liter | | | | |
| Median | 3.0 | 3.1 | 2.3 | 0.21 |
| Interquartile range | 1.2-6.7 | 1.3-7.3 | 1.0-5.9 | |

[1] Genotypes for 3 individuals were incomplete and did not allow determination of IL-1 (+) or 1 (−) status
[2] Mean ± standard deviation Influence of OxPL on CAD Risk is Mediated by IL-1 Genetic Differences Odds ratios for CAD in each quartile of OxPL/apoB were calculated in all patients, in IL-1(+) and IL-1(−) patients, and further analyzed by age (all ages, <60 years old and >60 years old). A significant association was present between increasing OxPL/apoB levels and risk for CAD in IL-1(+) patients [odds ratio (OR) 2.52, P=0.01 for fourth quartile compared to first quartile] whereas no significant relationship was present in IL-1(−) patients (Table 2). Interestingly, the genotype effect was strongly accentuated in IL-1(+) patients ≦60 years old (OR=6.92, P<0.001) but not in IL-1(−) patients ≦60 years old (OR=1.07, P=0.71]. In patients >60 years old, the association between OxPL/apoB levels and risk for CAD was not significant in either IL-1(+) or IL-1(−) patients. Nevertheless, when the two age strata were combined, the test of trend in the IL-1(+) group remained significant (P=0.01).

TABLE 2

Odds Ratios for CAD (>50% Diameter Stenosis) According to Quartiles for Oxidized Phospholipid:ApoB-100 Ratio in IL-1 Genotype Positive and IL-1 Genotype Negative Patients

| | Patient Group | | | | | | | | |
|---|---|---|---|---|---|---|---|---|---|
| | All Patients | | | IL-1 Genotype Positive | | | IL-1 Genotype Negative | | |
| | Total No. | No. with CAD (%) | OR (95% CI) | Total No. | No. with CAD (%) | OR (95% CI) | Total No. | No. with CAD (%) | OR (95% CI) |
| All ages | | | | | | | | | |
| Quartile I | 126[1] | 59 (47) | 1.00 | 78[2] | 37 (47) | 1.00 | 48 | 22 (46) | 1.00 |
| Quartile II | 125 | 65 (51) | 1.19 (0.73-1.96) | 73 | 35 (48) | 1.02 (0.54-1.93) | 51 | 28 (55) | 1.44 (0.65-3.18) |
| Quartile III | 126 | 68 (54) | 1.33 (0.81-2.18) | 76 | 38 (50) | 1.11 (0.59-2.09) | 49 | 29 (59) | 1.71 (0.77-3.83) |
| Quartile IV | 125 | 79 (63) | 1.95 (1.18-3.23) | 72 | 50 (69) | 2.52 (1.29-4.92) | 52 | 29 (56) | 1.49 (0.68-3.28) |
| P for trend | | | 0.009 | | | 0.01 | | | 0.29 |
| Age ≦60 yr | | | | | | | | | |
| Quartile I | 58 | 19 (33) | 1.00 | 32 | 8 (25) | 1.00 | 26 | 11 (42) | 1.00 |
| Quartile II | 53 | 17 (32) | 0.97 (0.44-2.15) | 32 | 9 (28) | 1.17 (0.39-3.57) | 21 | 8 (38) | 0.84 (0.26-2.72) |
| Quartile III | 60 | 27 (45) | 1.68 (0.79-3.55) | 41 | 17 (41) | 2.12 (0.77-5.85) | 19 | 10 (53) | 1.52 (0.46-4.98) |
| Quartile IV | 68 | 41 (60) | 3.12 (1.50-6.48) | 43 | 30 (70) | 6.92 (2.47-19.42) | 25 | 11 (44) | 1.07 (0.35-3.25) |
| P for trend | | | 0.001 | | | <0.001 | | | 0.71 |
| Age >60 yr | | | | | | | | | |
| Quartile I | 68 | 40 (59) | 1.00 | 46 | 29 (63) | 1.00 | 22 | 11 (5) | 1.00 |
| Quartile II | 72 | 47 (65) | 1.32 (0.66-2.61) | 41 | 26 (63) | 1.02 (0.42-2.43) | 30 | 20 (67) | 2.00 (0.65-6.19) |
| Quartile III | 66 | 41 (62) | 1.15 (0.57-2.30) | 35 | 21 (60) | 0.88 (0.36-2.17) | 30 | 19 (63) | 1.73 (0.56-5.28) |
| Quartile IV | 57 | 38 (67) | 1.40 (0.67-2.91) | 29 | 20 (69) | 1.30 (0.48-3.50) | 27 | 18 (67) | 2.00 (0.63-6.36) |
| P for trend | | | 0.46 | | | 0.74 | | | 0.33 |

[1]Two subjects were missing OxPL values, leaving 502 subjects for analyses that did not involve IL-1 genotypes
[2]Genotype for 3 individuals were incomplete and did not allow determination of IL-1(+) or IL-1(−) status, leaving a total of 499 subjects available for analyses that included both OxPL values and IL-1 genotypes Similar to the OxPL/apoB results, the association between Lp(a) and risk for CAD was observed primarily in IL-1(+) patients (Table 3), with the strongest genotype effect present in patients ≦60 years of age (OR 9.0, P<0.001).

TABLE 3

Odds Ratios for CAD (>50% Diameter Stenosis) According to Quartiles of Lp(a) Lipoprotein in IL-1 Genotype Positive and IL-1 Genotype Negative Patients

| | Patient Group | | | | | | | | |
|---|---|---|---|---|---|---|---|---|---|
| | All Patients | | | IL-1 Genotype Positive | | | IL-1 Genotype Negative | | |
| | Total No. | No. with CAD (%) | OR (95% CI) | Total No. | No. with CAD (%) | OR (95% CI) | Total N | No. with CAD (%) | OR (95% CI) |
| All ages | | | | | | | | | |
| Quartile I | 126 | 56 (44) | 1.00 | 71 | 31 (44) | 1.00 | 55 | 25 (45) | 1.00 |
| Quartile II | 126 | 62 (49) | 1.21 (0.74-1.99) | 77 | 37 (48) | 1.19 (0.62-2.28) | 48 | 42 (50) | 1.20 (0.55-2.61) |
| Quartile III | 127 | 70 (55) | 1.54 (0.94-2.52) | 84 | 42 (50) | 1.29 (0.68-2.43) | 42 | 27 (64) | 2.16 (0.95-4.93) |
| Quartile IV | 125 | 83 (66) | 2.47 (1.48-4.12) | 68 | 51 (75) | 3.87 (1.88-7.97) | 56 | 32 (57) | 1.60 (0.76-3.39) |
| P for trend | | | <0.001 | | | <0.001 | | | 0.12 |
| Age ≦60 yr | | | | | | | | | |
| Quartile I | 60 | 18 (30) | 1.00 | 32 | 8 (25) | 1.00 | 28 | 10 (36) | 1.00 |
| Quartile II | 57 | 19 (33) | 1.17 (0.53-2.54) | 36 | 10 (28) | 1.15 (0.39-3.41) | 21 | 9 (43) | 1.35 (0.42-4.30) |
| Quartile III | 58 | 28 (48) | 2.18 (1.02-4.63) | 44 | 19 (43) | 2.28 (0.84-6.19) | 14 | 9 (64) | 3.24 (0.85-12.36) |
| Quartile IV | 64 | 39 (61) | 3.64 (1.73-7.68) | 36 | 27 (75) | 9.00 (3.00-27.03) | 28 | 12 (43) | 1.35 (0.46-3.96) |
| P for trend | | | 0.001 | | | <0.001 | | | P = 0.43 |
| Age >60 yr | | | | | | | | | |
| Quartile I | 66 | 38 (58) | 1.00 | 39 | 23 (59) | 1.00 | 27 | 15 (56) | 1.00 |
| Quartile II | 69 | 43 (62) | 1.22 (0.61-2.43) | 41 | 27 (66) | 1.34 (0.54-3.33) | 27 | 15 (56) | 1.00 (0.34-2.93) |
| Quartile III | 69 | 42 (61) | 1.15 (0.58-2.28) | 40 | 23 (58) | 0.94 (0.38-2.30) | 28 | 18 (64) | 1.44 (0.49-4.25) |
| Quartile IV | 61 | 44 (72) | 1.91 (0.91-4.01) | 32 | 24 (75) | 2.09 (0.75-5.81) | 28 | 20 (71) | 2.00 (0.65-6.11) |
| P for trend | | | P = 0.13 | | | P = 0.31 | | | P = 0.18 |

Further Characterization of CAD Risk in the Different Genetic Strata: To explore further the relationship between OxPL/apoB or Lp(a) levels and IL-1 genotype relative to risk for CAD, patients were stratified by IL-1 genotype and developed regression models to assess the relationship of OxPL/apoB and Lp(a) levels to CAD risk. In this model, the delta OxPL/apoB and delta Lp(a) represent the difference in values between any 2 quartiles of OxPL/apoB or Lp(a) and the corresponding OR for CAD. The relationship of the OR values for CAD is expressed as function of the magnitude of differences in OxPL/apoB and Lp(a) levels in IL-1(+) and IL-1(−) patients (FIG. 1). The OR for CAD was highly sensitive to differences in levels of both OxPL/apoB and Lp(a) in IL-1(+) patients, but no association was present in IL-1(−) patients.

In addition to univariate analysis, multivariate logistic regression was performed to adjust for factors known to affect risk of CAD. FIG. 2 shows ORs for gender, age, LDL, HDL, triglycerides, hypertension, CRP, Lp(a), and OxPL/apoB ratio when all are included in a single regression model. In IL-1(+) patients $\leq 60$ years old, OxPL/apoB ratio (log2), male gender, age per decade and CRP were independent predictors of CAD, whereas Lp(a) was not a significant predictor once the OxPL/apoB ratio was included in the model (FIG. 2A). In IL-1(−) patients $\leq 60$ years old, the OxPL/apoB ratio was not a predictor of CAD, but gender, LDL cholesterol, and hypertension were independent predictors (FIG. 2B). In subjects >60 years old, gender remained a significant predictor of CAD in both IL-1(+) and IL-1(−) subjects and hypertension was significant in IL-1(−) subjects (FIGS. 2C and 2D). OxPL/apoB and Lp(a) were not significant predictors of CAD in either IL-1(+) or IL-1(−) patients >60 years old. When the 41 patients with myocardial infarction within 60 days prior to coronary angiography were excluded, the data remained qualitatively similar, except that CRP was no longer a predictor of CAD. Baseline CRP levels in these patients were significantly elevated compared to patients without myocardial infarction.

Notably, among IL-1(+) individuals $\leq 60$ years old, Lp(a) did not retain significance when the OxPL/apoB ratio was placed in the model. Additionally, the OxPL ratio is significantly associated with CAD in those above (OR=1.93, P=0.02) and below (OR=2.06, P=0.03) the median Lp(a) value, whereas this relationship is not present for Lp(a) when the population is stratified by the median OxPL ratio/apoB ratio.

IL-1 Genotype Effect on OxPL Risk for CAD is not Mediated by C-Reactive Protein Levels: Since some of the IL-1 gene variations included in the genetic patterns used in this study have been associated with elevated CRP, an evaluation of whether the IL-1 genotype influences the OxPL association with CAD was attributable to CRP was performed. The relationship of OxPL/apoB to CAD in IL-1 (+) individuals was analyzed in the multivariate logistic regression framework for patients with CRP above and below the median CRP level in this study population (3 mg/L). The OxPL/apoB association with CAD in IL-1(+) patients was comparable in patients with CRP >3 mg/L [OR(95% CI) 2.3(1.1-5.1), P=0.02] and in those with CRP <3 mg/L [OR 3.2(1.1-10.3, P=0.02], indicating that the OxPL interaction with IL-1 genotype is not a function of CRP levels. Similar results were obtained for Lp(a) in IL-1(+) patients stratified by CRP levels. The association of OxPL/apoB and Lp(a) to CAD remained similar with and without CRP in the model.

Relationship of IL-1 Genotype to Age at Presentation to the Cardiac Catheterization Laboratory: Having established the relationship of the OxPL/apoB ratio and Lp(a) with CAD in IL-1(+) but not IL-1(−) individuals, a search for another clinical features that may be impacted by the IL-1 composite genotype was performed. One such feature is age at presentation to the cardiac catheterization laboratory. IL-1(+) patients in upper two quartiles of OxPL/apoB presented to the cardiac catheterization laboratory a mean of 4.3 years younger than IL-1(−) patients (P=0.002). Similarly, IL-1(+) patients in the upper two quartiles of Lp(a) presented a mean of 3.5 years younger than IL-1(−) patients (P=0.01). In contrast, there was no significant IL-1 genotype effect on the age at presentation to the cardiac catheterization laboratory for patients in the lowest two quartiles of OxPL/apoB (P=0.14) or Lp(a) (P=0.40). In addition, there was a strong trend toward higher prevalence of prior myocardial infarction in IL-1(+) genotype (P=0.08).

This study demonstrates that IL-1 genetic differences that are known to be associated with inflammatory responsiveness strongly influence the risk of CAD mediated by OxPL/apoB and Lp(a). Patients with pro-inflammatory IL-1(+) genotypes were at a continuum of risk for the presence of CAD, defined as >50% diameter stenosis, whereas patients with IL-1(−) genotypes seemed to be insensitive to risk for CAD mediated by increasing OxPL/apoB or Lp(a) levels. These findings were independent of CRP levels suggesting that this influence on CAD is a more proximal effect on the inflammatory cascade. This study provides evidence of a plausible biological link between genetic predisposition to inflammation, lipid disorders, oxidation of lipoproteins and clinically manifest CAD and highlights a possible effect of specific genetic factors in accelerating or attenuating atherogenesis.

The genes encoding the pro-inflammatory cytokines interleukin-1 alpha and interleukin-1 beta are among the first to be activated in the course of an inflammatory response, and play a major role in both acute and chronic inflammation. Plasma levels of IL-1 alpha and IL-1 beta show reproducible interindividual differences. Furthermore, IL-1 gene patterns that are highly prevalent in the population, 60% of Caucasians as noted in this study, have been associated with variations in the levels or expression of IL-1 alpha, IL-1 beta and the endogenous antagonist, IL-1 receptor antagonist (IL-1ra). The IL-1 composite genotypes used in this study were derived from combinations of the predominant functional haplotypes in the promoter region of the gene for IL-1 beta and other SNPs in the IL-1 alpha and beta genes that have been associated with pro-inflammatory responses. IL-1 beta haplotypes exhibit allele-specific differences in nuclear protein binding and transcription rates. IL-1(+) genotypes are associated with enhanced generation of IL-1 beta when mononuclear cells are stimulated and have been associated with higher IL-1 beta levels in plasma. Some of the three composite genotypes that comprise the IL-1(+) pattern for this study have been associated with significantly elevated CRP levels in plasma compared with IL-1(−) pattern but for the total IL-1(+) group CRP was not significantly higher in this study. It should be noted that although the IL-1 genotype association with elevated IL-1 beta expression is also significant in gastric mucosa, the genotypes associated with elevated expression appear to be different from those reported for peripheral blood mononuclear cells. In addition, the genotype associations with disease in this study and with inflammatory mediators in other studies are in Caucasian populations, and the IL-1 genotype associations may differ in other ethnic populations.

IL-1 is produced by monocytes, macrophages, endothelial cells, and smooth muscle cells and is actively expressed in atherosclerotic plaques and activates biological pathways within the arterial wall that are implicated in the development of atherosclerosis. In IL-1 receptor antagonist knockout mice, unopposed IL-1 biological activity resulted in spontaneous arterial inflammation with massive infiltration of macrophages and CD4+, interferon gamma+ T-cells at branch points in mid and large arteries. Decreases in IL-1 biological activity in apoE-deficient mice decreased the rate and extent of atherosclerosis formation. In contrast, increases in IL-1 activity increased atherosclerotic lesion size with more macrophages within lesions.

In experimental studies, oxidized phospholipids interact with cells in the vessel wall and promote pro-inflammatory and pro-atherogenic properties. In support of this concept, plasma levels of OxPL/apoB strongly predict the presence of coronary, carotid and femoral artery disease as well as the potential destabilization of vulnerable plaques. Interestingly, studies show that in humans most OxPL detected by antibody E06 (>90%) are actually present on Lp(a), rather than other apoB-containing lipoproteins. The strong association of OxPL/apoB and Lp(a), along with the fact that Lp(a) levels are genetically determined, suggests that a potential physiological role of Lp(a) may be to bind, transport and potentially detoxify pro-inflammatory OxPL. This is supported by the observation that Lp(a) is enriched in the enzyme platelet-activating factor acetylhydrolase (PAF-ACH), which cleaves the oxidized fatty acid from oxidized phospholipids, and that lower activity of PAF-ACH on Lp(a) particles is associated with higher risk of CAD.

OxPL/apoB and Lp(a) levels generally provided similar power in predicting cardiovascular disease, except in patients <60 years old where additional risk of OxPL/apoB was present independent of Lp(a) levels. This study has expanded the understanding of the underlying mechanisms behind this risk by showing that the enhanced risk of CAD mediated by OxPL/apoB and Lp(a) only seems to be present in IL-1 (+) patients. Interestingly, this risk persisted despite Lp(a) in the model, suggesting that in certain patient populations, such as patients <60 years old, OxPL/apoB may be a better predictor than Lp(a), perhaps through additional pro-inflammatory properties. Patients with underlying genetic predisposition to pro-inflammatory and lipid risk factors have exposure to cardiovascular risk from birth, which may explain why IL-1(+) patients ≦60 years old with elevated Lp(a) and OxPL/apoB levels are at particularly elevated risk for premature CAD. Consistent with the role of life-long exposure to genetic predisposition to inflammation and genetically determined Lp(a) levels, it was demonstrated in this study that IL-1(+) patients with Lp(a) or OxPL/apoB levels in the highest 2 quartiles presented for coronary angiography significantly earlier than those in the lowest quartiles. In a similar manner, subjects with life-long lower LDL-cholesterol levels have disproportionately lower risk of CAD than predicted from models in adult patients.

It is noteworthy that, in this population, the IL-1 genotype effect on risk of CAD was not attributable to CRP, which is generally thought to be a biomarker of inflammation generated secondary to cytokines such as IL-6 and IL-1. However, the effects of OxPL have been shown to be pro-inflammatory at the level of various cells of the arterial intima. For example, in a large-scale gene expression analysis involving 9,600 cDNA targets, IL-1 beta was one of the differentially overexpressed genes when macrophages were loaded with OxLDL, which is known to be enriched in OxPL detected by E06, compared to acetylated-LDL loading. OxLDL stimulation of coronary artery smooth muscle cells also led to significant over-expression of IL-1 beta. Thus, it is reasonable to hypothesize that the polymorphisms of the IL-1 family might influence the expression of inflammatory responses to OxPL.

Indeed, supporting data shows that IL-1 genetic variations have been associated with acute coronary events, CAD and stroke.

Limitations of this study include that patients were selected from a symptomatic population referred for coronary angiography and the data may not be generalized to broader populations. This study also included predominantly Caucasian patients whose genetic associations may differ in other ethnic groups and therefore it will be important to test these associations in other populations.

The study demonstrates that the contribution of OxPL/apoB and Lp(a) on angiographically documented CAD is conditional on pro-inflammatory IL-1 genotypes. This novel paradigm links the etiology of atherogenesis attributed to OxPL/apoB and Lp(a) from genetics to clinical expression of CAD. These findings facilitate the understanding of atherogenesis and provide enhanced tools for diagnosis and treatment of cardiovascular disease.

Example 2

The study population was recruited as a sex- and age-stratified random sample of all inhabitants of Bruneck, Italy (125 women and 125 men in the 5th to 8th decades each, n=1000). At the 1990 baseline, 93.6% of recruited subjects participated, with data assessment completed in 919 subjects. The current study focuses on the 1995 re-examination and the follow-up period for clinical events between 1995 and 2005. In 1995, the study population still consisted of 826 subjects (96.5 percent of those alive) and plasma samples for assessment of OxPL/apoB and Lp(a) were available in a random sub-sample of 765 subjects. Detailed information about cardiovascular events developing between 1995 and 2005 was available in all of these subjects (100% follow-up). The study protocol was approved by the appropriate ethics committees and all study subjects gave their written informed consent before entering the study.

The content of OxPL per apoB-100 particle (OxPL/apoB) was measured as previously described in detail by chemiluminescent ELISA using the murine monoclonal antibody E06, which binds to the phosphorylcholine (PC) headgroup of oxidized but not native phospholipids. As previously described, equal numbers of apoB-100 particles are captured from each plasma sample and thus the content of OxPL is normalized for apoB-100 in each subject. Thus, by design, the OxPL/apoB measurement is independent of apoB-100 (and LDL-cholesterol) levels. It is to be emphasized that the "apoB" measure depicted in the denominator of the OxPL/apoB parameter does not represent the plasma apoB level, but instead reflects the amount of apoB captured on each microtiter well plate. The intra and inter-assay coefficients of variation were: OxPL/apoB: 6-10%, 6 Lp(a): 3.6-6.3% and apoB-100: 2.4%.

The enzyme Lp-PLA2, also known as platelet activating factor acetylhydrolase, cleaves oxidized fatty acid moieties at the sn-2 position of OxPL to generate a free oxidized fatty acid and lysophosphatidylcholine. Lp-PLA2 activity was measured with a commercially available kit (Azwell Inc., Osaka, Japan) based on the method of Kosaka et al. Reference normal values are <800 IU/L(μmol/min/L) as given by the manufacturer.

In the primary analysis the CVD endpoint comprised all incident cases of cardiovascular death, myocardial infarction, ischemic stroke and transient ischemic attack TIA (n=82). Sensitivity analyses focused on individual diseases and extended composite outcomes. Extended composite endpoints additionally included revascularization procedures which increased the number of individuals affected from 82 to 98 and new onset symptomatic peripheral arterial disease which further increased the number of individuals affected from 98 to 108. Myocardial infarction was deemed confirmed when World Health Organization criteria for definite disease status were met. Stroke and TIA were classified according to the criteria of the National Survey of Stroke. The diagnosis of symptomatic peripheral arterial disease required a positive response to the Rose questionnaire (typical claudication), with the vascular nature of complaints confirmed by standard diagnostic procedures (ankle-brachial pressure index or angiography), or an acute peripheral artery occlusion requiring revascularization. All other revascularization procedures (angioplasty and surgery) were carefully recorded. Ascertainment of events or procedures did not rely on hospital discharge codes or the patient's self-report but on a careful review of medical records provided by the general practitioners and files of the Hospital and the extensive clinical and laboratory examinations performed as part of the study protocols.

All calculations were performed using the SPSS 12.0 and BMDP software packages. Continuous variables were presented as means±SD or medians (interquartile range), and dichotomous variables as percentages. Differences in baseline levels of vascular risk attributes between subjects with and without subsequent CVD (1995 to 2005) were analyzed with the Student's t-test and $\chi 2$-test. Variables with a skewed distribution were loge-transformed to satisfy the assumption of normality and constant variance of the residuals. Cox proportional hazard models were used to assess whether baseline OxPL/apoB levels were independent risk predictors for incident CVD. For this purpose OxPL/apoB was either modeled as a categorical (tertile or sextile groups) or as a continuous variable. Several models were run: the first one included age, sex, previous cardiovascular disease and OxPL/apoB; the second model was additionally adjusted for systolic blood pressure, smoking, diabetes, ferritin level, fibrinogen level, LDL-C and HDL-C, waist-hip ratio, alcohol consumption, social status, sports activity, and loge-transformed level of hsCRP, urinary albumin, uric acid, loge-transformed α1-antithrypsin, loge-transformed homeostasis model of insulin resistance (HOMA-IR) and Lp-PLA2 activity. ApoB was not included because of the high correlation with LDL-C and potential problem of collinearity. If apoB was used instead of LDL-C, however, results remained virtually unchanged. Furthermore, alternative models built by a forward stepwise selection procedure (allowing for all variables in Table 5) yielded very similar results with respect to the OxPL/apoB—CVD association; the third model included previous cardiovascular disease, the Framingham Risk Score and loge-transformed level of hsCRP. To test for linear trend, we used the median level in each tertile group of OxPL/apoB as a continuous variable. All analyses were repeated with Lp(a) concentration included instead of OxPL/apoB level. Proportional hazard assumptions were tested for OxPL/apoB and Lp(a) and satisfied in all models. Differential associations in subgroups were analysed by inclusion of appropriate interaction terms. All reported P values are two-sided.

Baseline demographic, clinical and laboratory characteristics of the study subjects in 1995 are shown in Table 5. All subjects are of Caucasian origin. The data are presented for subjects with (CVD+) and without (CVD−) incident (future) CVD over the 10 year follow-up period. Subjects with incident CVD had increased baseline levels of OxPL/apoB, Lp(a) and Lp-PLA2 activity (Table 5). As expected, subjects with incident CVD were more likely to be older, male, physically inactive and had higher levels of systolic blood pressure, homeostasis model of insulin resistance (HOMA-IR), waist-to-hip ratio, urinary albumin (microalbuminuria), uric acid, fasting glucose, total cholesterol, LDL-C, apoB-100, fibrinogen and hsCRP (Table 5). Subjects with future CVD events also had a higher prevalence of pre-existing CVD.

Levels of OxPL/apoB and Lp(a) were highly correlated (r=0.87, P<0.001) whereas weak correlations emerged between OxPL/apoB and Lp-PLA2 activity (r=0.074, P=0.040), and Lp(a) and Lp-PLA2 activity (r=0.065, P=0.072).

TABLE 5

Table 5. Characteristics of study subjects (n = 765).

| | Mean ± SD, Median (IQR) * or % | | |
|---|---|---|---|
| Variable | CVD−<br>(n = 683) | CVD+<br>(n = 82) | P<br>value |
| Age (yr) | 61.8 ± 10.9 | 70.2 ± 10.3 | <0.001 |
| Female sex (%) | 51.0% | 37.8% | 0.024 |
| OxPL/apoB* | 0.051 (0.033-0.125) | 0.070 (0.040-0.224) | 0.008 |
| Lipoprotein(a) (mg/dl)* | 11.6 (4.5-34.4) | 20.8 (7.7-50.5) | 0.010 |
| Lp-PLA2 activity (μmol/min/L) | 770.7 ± 192.1 | 884.1 ± 196.0 | <0.001 |
| Vascular risk factors: | | | |
| Hypertension (%) | 67.5% | 69.5% | 0.71 |
| Systolic BP (mmHg) | 147.4 ± 20.3 | 152.3 ± 22.4 | 0.041 |
| Diastolic BP (mmHg) | 86.9 ± 9.0 | 87.1 ± 9.5 | 0.83 |
| Current smoking (%) | 20.1% | 18.3% | 0.71 |
| Smoking (cigarettes/d) | 2.6 ± 6.1 | 2.8 ± 7.1 | 0.72 |
| Diabetes (WHO) (%) | 8.8% | 14.6% | 0.087 |
| Fasting glucose (mg/dl) | 101.7 ± 24.6 | 108.0 ± 28.3 | 0.033 |
| Ferritin (μg/liter) | 131.6 ± 153.2 | 163.8 ± 171.0 | 0.076 |
| HOMA-IR* | 1.98 (1.41-2.96) | 2.4 (1.65-4.05) | 0.022 |
| Microalbuminuria (g/liter)* | 9.0 (7.0-16.0) | 11.5 (8.0-54.8) | 0.003 |
| Uric acid (mg/dl) | 4.7 ± 1.3 | 5.1 ± 1.4 | 0.006 |
| Coagulation: | | | |
| Fibrinogen (mg/dl) | 285.9 ± 72.8 | 307.0 ± 70.6 | 0.013 |
| Antithrombin III (%) | 99.6 ± 11.5 | 97.3 ± 11.6 | 0.094 |
| Activated protein C ratio | 3.2 ± 0.6 | 3.1 ± 0.6 | 0.12 |

TABLE 5-continued

Table 5. Characteristics of study subjects (n = 765).

| Variable | Mean ± SD, Median (IQR) * or % | | P value |
|---|---|---|---|
| | CVD− (n = 683) | CVD+ (n = 82) | |
| Lipids and lipoproteins: | | | |
| Total cholesterol (mg/dl) | 228.4 ± 42.0 | 240.7 ± 43.8 | 0.013 |
| Triglycerides (mg/dl)* | 109 (80-157) | 118 (90-164) | 0.23 |
| HDL cholesterol (mg/dl) | 59.2 ± 16.2 | 56.9 ± 18.2 | 0.24 |
| LDL cholesterol (mg/dl) | 143.8 ± 37.5 | 155.8 ± 39.5 | 0.007 |
| LDL cholesterol corr‡(mg/dl) | 135.2 ± 36.6 | 142.4 ± 38.8 | 0.093 |
| Apolipoprotein A-I (mg/dl) | 166.2 ± 27.4 | 164.9 ± 29.7 | 0.70 |
| Apolipoprotein B-100 (mg/dl) | 114.6 ± 30.9 | 124.9 ± 33.6 | 0.005 |
| Infection and inflammation: | | | |
| $\alpha_1$antithrypsin (mg/dl) | 197.4 ± 36.9 | 206.6 ± 33.0 | 0.031 |
| C-reactive protein (mg/liter) | 2.7 ± 7.1 | 3.7 ± 6.6 | 0.030 |
| Nutrition, activity and body composition: | | | |
| Sports index (Beacke)$_{34}$ | 2.4 ± 0.9 | 2.1 ± 0.8 | 0.001 |
| Energy intake (Kcal) | 2836 ± 871 | 2782 ± 810 | 0.59 |
| Fat intake (g/day) | 148.0 ± 48.6 | 145.2 ± 45.3 | 0.62 |
| Alcohol (g/day) | 4.0 ± 31.4 | 23.9 ± 29.4 | 0.98 |
| Body-mass index (kg/m$_2$) | 25.6 ± 3.7 | 26.0 ± 4.5 | 0.30 |
| Waist-hip ratio (cm/cm) | 0.928 ± 0.071 | 0.948 ± 0.075 | 0.017 |
| Pre-existent CVD: | | | |
| CVD$_§$ (%) | 8.2% | 25.6% | <0.001 |

Figure 3:
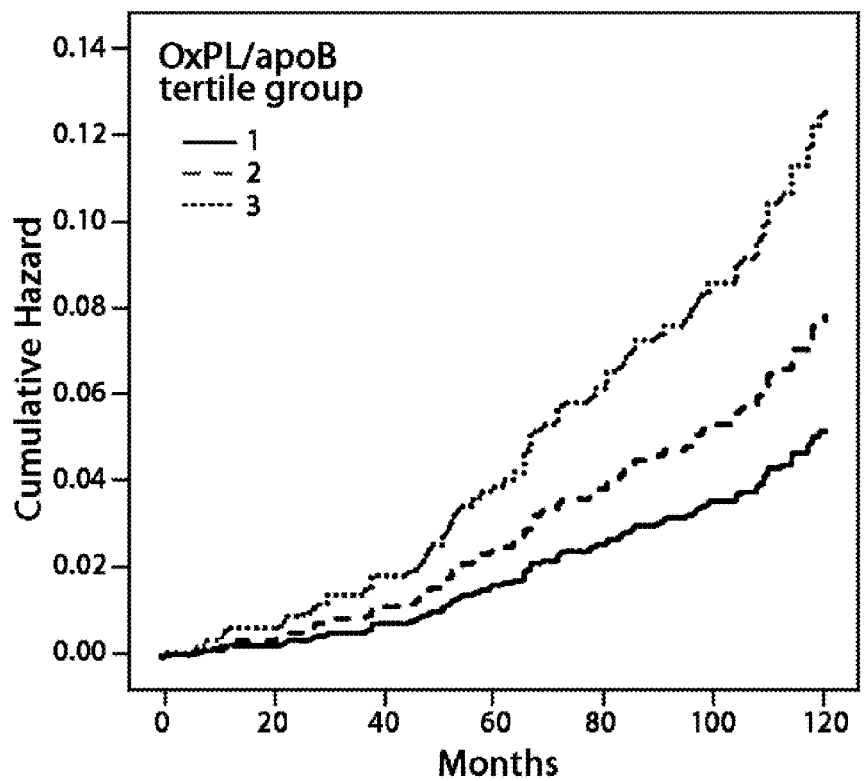
FIG. 3A-B shows cumulative hazard curves (model 2) of incident CVD from 1995-2005 for tertiles of OxPL/apoB (A) and Lp(a) (B).
Figure 3:
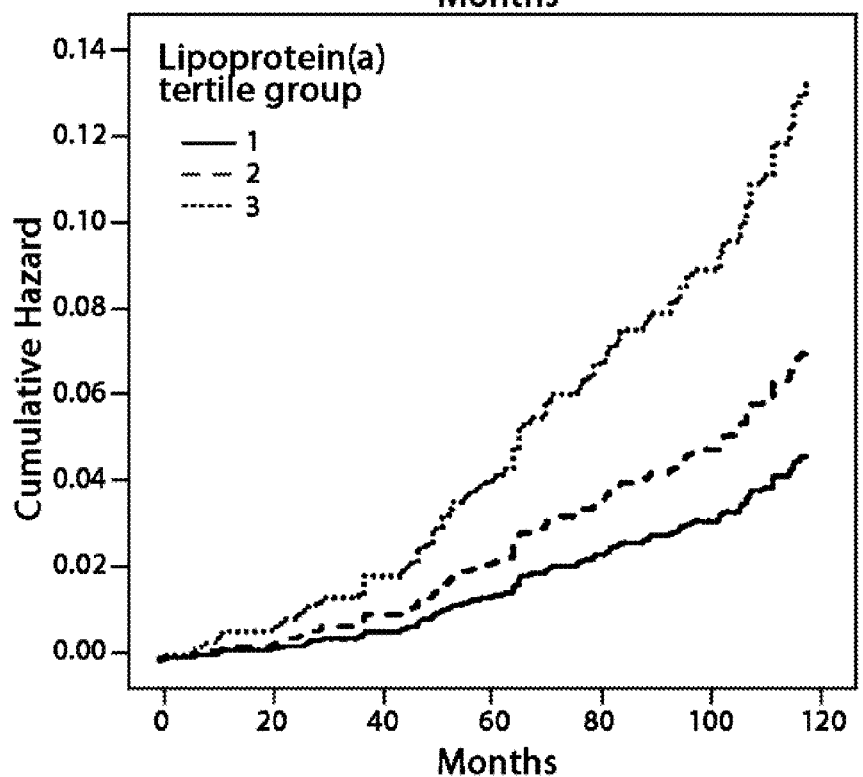
Figure 4:
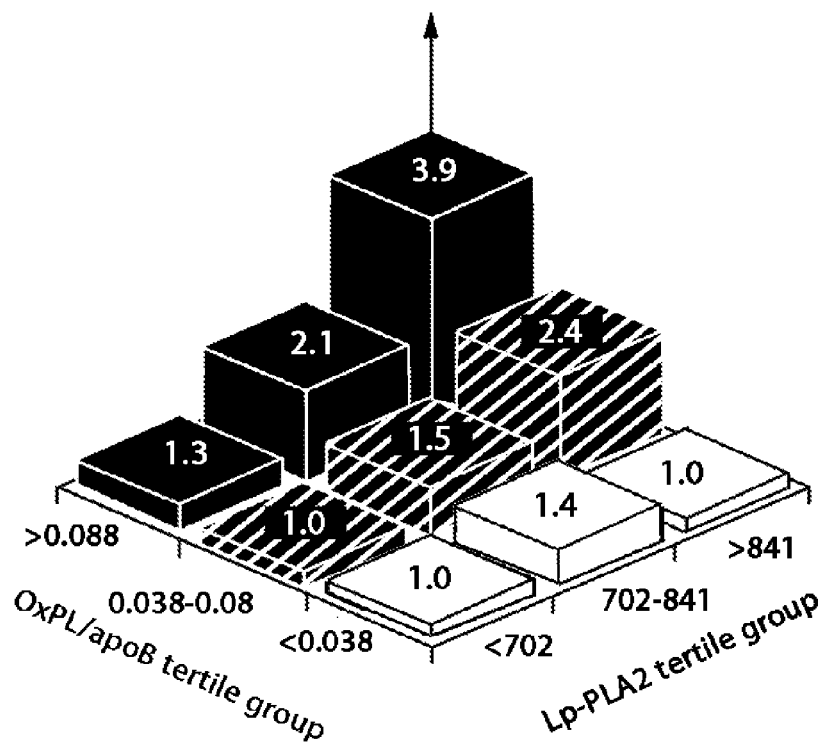
FIG. 4A-B shows a relationship between OxPL/apoB (A), and Lp(a) (B) tertile groups and CVD risk according to tertiles of Lp-PLA2 activity (P=0.018 and P=0.008 for interaction of OxPL/apoB and Lp(a), respectively).
Figure 4:
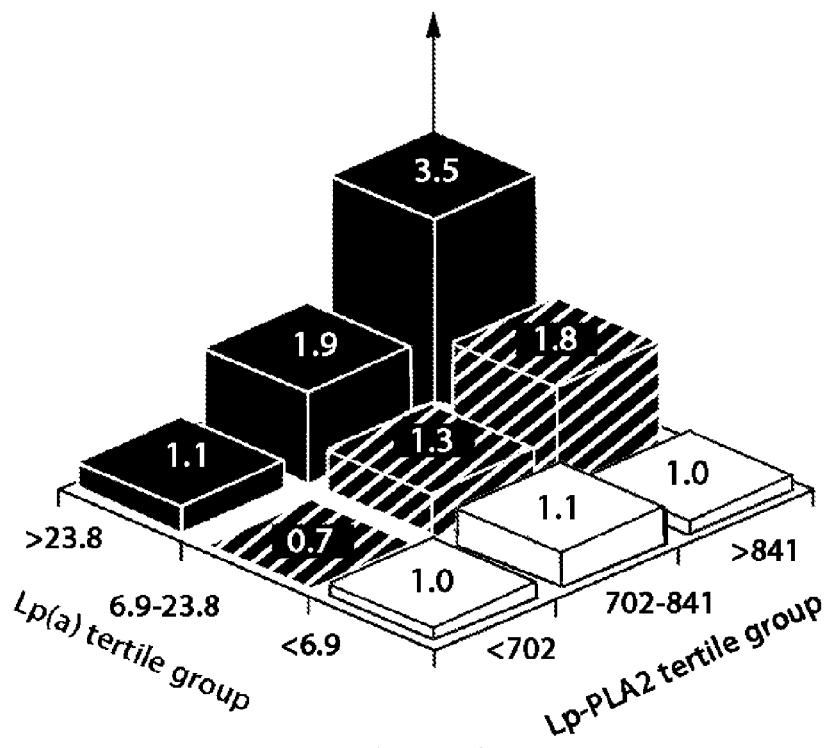

In Cox regression analysis, the risk of incident CVD gradually increased across tertile groups for OxPL/apoB and Lp(a) level (Table 6). This finding applied to base models adjusted for age, sex and previous cardiovascular disease [model 1; hazard ratio (HR) [95% CI] 1.6[0.9-2.9] and 2.3[1.3-4.1], P=0.005 for trend for OxPL/apoB, and HR 1.4[0.8-2.6] and 2.6[1.4-4.6] P<0.001 for trend for Lp(a), both for comparison between the middle and highest vs. lowest tertile group], and to multivariable models additionally adjusted for a broad palette of established and putative vascular risk factors [model 2; HR 1.5[0.8-2.8] and 2.4[1.3-4.3], P=0.004 for trend for OxPL/apoB and HR 1.5[0.8-2.8] and 2.8[1.6-5.0], P<0.001 for trend for Lp(a) (Table 2)]. Cumulative hazard plots (model 2) are depicted in FIG. 3 and indicate a progressive divergence in event frequency in OxPL/apoB and Lp(a) across tertiles. Lp-PLA2 activity was also a significant risk predictor of CVD in model 2 (HR[95% CI] for a 1-SD unit increase 1.4[1.1-1.4], P=0.008). Of interest, the strength of the association between OxPL/apoB and Lp(a) and CVD risk significantly increased with increasing Lp-PLA2 activity (P=0.018 and P=0.008, respectively, for interaction) (FIG. 4).

TABLE 6

Table 2. Hazard ratios (HRs) of incident myocardial infarction, stroke and TIA (1995-2005) by tertile groups for OxPL/apoB and Lp(a) (n = 765)

| | Cases n | Non-cases n | Model 1 | Model 2 |
|---|---|---|---|---|
| OxPL/apoB [ratio] | | | | |
| Tertile 1 [<0.0379] | 18 | 237 | 1.0 (Reference) | 1.00 (Reference) |
| Tertile 2 [0.0379-0.0878] | 26 | 229 | 1.6 (0.9-2.9) | 1.5 (0.8-2.8) |
| Tertile 3 [>0.0878] | 38 | 217 | 2.3 (1.3-4.1) | 2.4 (1.3-4.3) |
| P for trend | | | 0.005 | 0.004 |

TABLE 6-continued

Table 2. Hazard ratios (HRs) of incident myocardial infarction, stroke and TIA (1995-2005) by tertile groups for OxPL/apoB and Lp(a) (n = 765)

| | Cases n | Non-cases n | Model 1 | Model 2 |
|---|---|---|---|---|
| Lipoprotein(a) [mg/dl] | | | | |
| Tertile 1 [<6.9] | 18 | 236 | 1.00 (Reference) | 1.00 (Reference) |
| Tertile 2 [6.9-23.9] | 24 | 232 | 1.4 (0.8-2.6) | 1.5 (0.8-2.8) |
| Tertile 3 [≧24.0] | 40 | 215 | 2.6 (1.4-4.6) | 2.8 (1.6-5.0) |
| P for trend | | | <0.001 | <0.001 |

Figure 5:
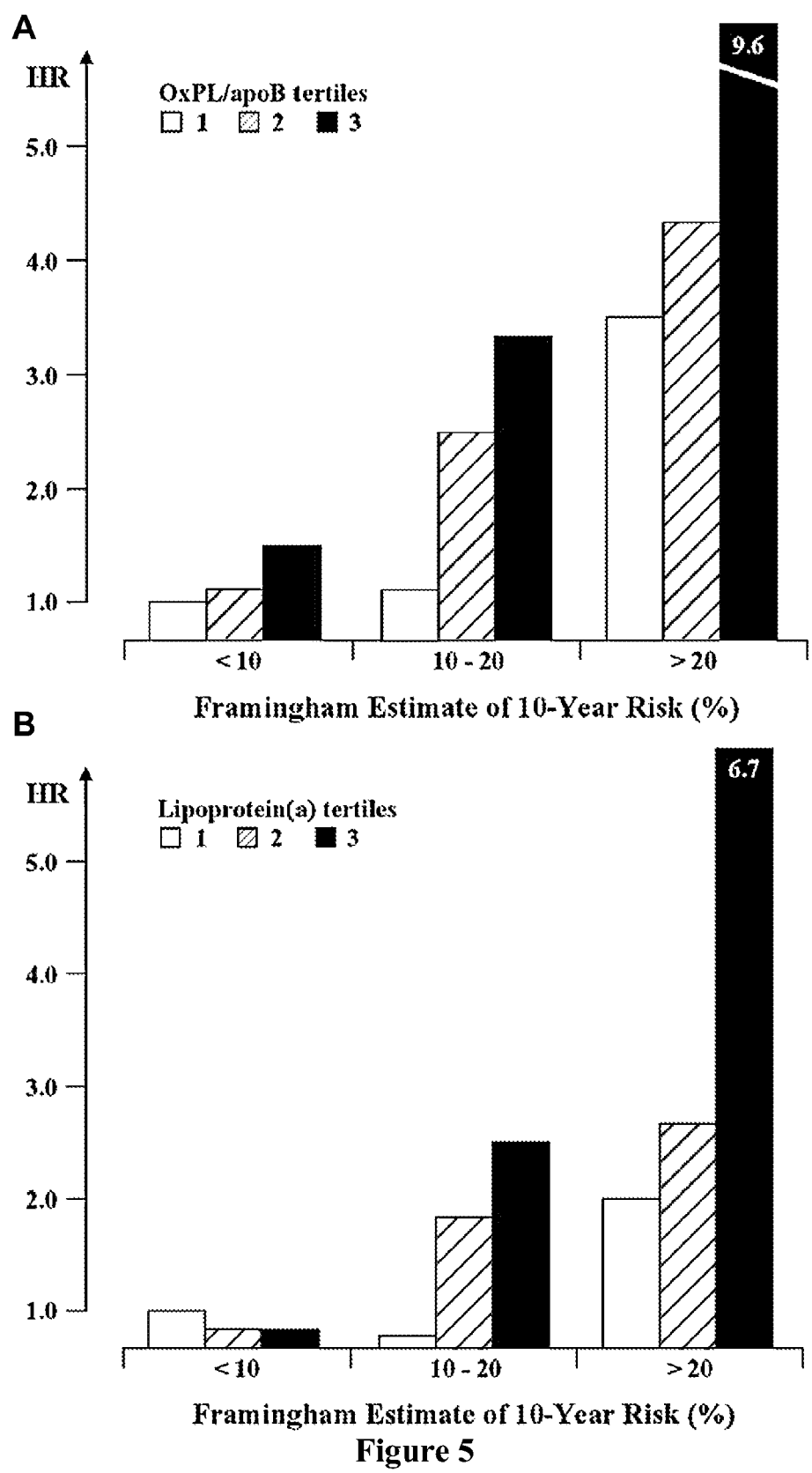
FIG. 5A-B shows a relationship between tertile groups of OxPL/apoB (A) (<0.0379, 0.0379-0.0878, >0.0878), and Lp(a) (B) (<6.9, 6.9-23.8, >23.8) (B) and CVD risk within each Framingham Risk Score Group. Framingham Risk Score was calculated as low risk (<10% risk of events over 10 years), moderate risk (10%-20%) and high risk (>20%).

Alternative models adjusted for the Framingham Risk Score, log$_e$-transformed hsCRP, and prior CVD yielded nearly identical results (HR 2.2[1.2-3.8] and 1.4[0.8-2.5]) for a comparison of the highest and middle, respectively, vs. bottom tertile group for OxPL/apoB (P=0.006 for trend) and 2.3[1.3-4.0] and 1.2[0.7-2.3] for a comparison of the highest and middle vs. bottom tertile group for Lp(a) (P=0.001 for trend). As visualized in FIG. 5A, the graded increase in CVD risk across OxPL/apoB tertile groups was evident in the low risk, moderate risk and high risk groups as defined by the Framingham Risk Score. Findings were similar but less consistent for Lp(a) tertile groups (FIG. 5B).

Figure 7:
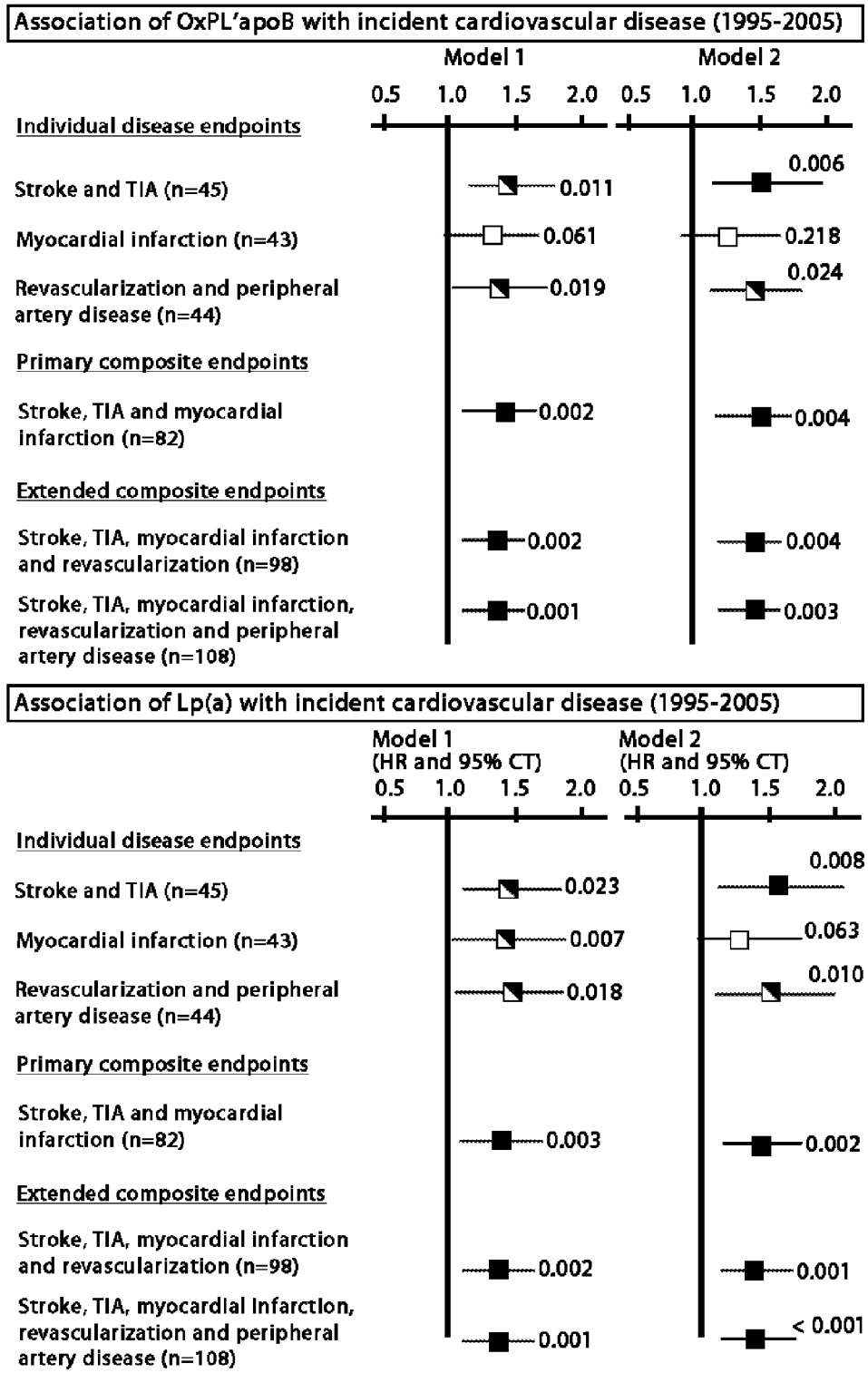
FIG. 7 shows an association of OxPL/apoB and Lp(a) with incident cardiovascular disease (1995-2000). Squares, lines and numbers are hazard ratios (HRs), 95% confidence intervals and P values.

The associations of OxPL/apoB and Lp(a) with CVD were consistent in five additional sensitivity analyses: (1) When OxPL/apoB and Lp(a) were treated as continuous variables, HR [95% CIs] calculated for a 1-SD unit increase in log$_e$-transformed variable levels were 1.4[1.1-1.7] (P=0.002) and 1.4[1.1-1.8] (P=0.003), respectively, in model 1 and 1.4[1.1-1.7] (P=0.004) and 1.4[1.1-1.8] (P=0.003), respectively, in model 2. When both OxPL/apoB and Lp(a) were entered into the same model (stepwise selection) OxPL/apoB was slightly superior to Lp(a) in predicting cardiovascular events but they were not independent of each other; (2) Exclusion of the 77 subjects with pre-existent CVD had little effect on the results (HR 2.3[1.1-4.6] and 1.9[0.9-3.8] for a comparison of the highest and middle vs. bottom tertile group for OxPL/apoB, P for trend 0.049). There was no differential effect of OxPL/apoB on CVD in this group (HR[95% CI] for a 1-SD unit increase in loge-transformed OxPL/apoB 1.3[1.1-1.7]; P=0.017) and in subjects with pre-existent disease (HR[95% CI] for a 1-SD unit increase in loge-transformed OxPL/apoB 1.3[1.0-2.1], P=0.085); (3) In subgroup analyses, the association tended to be slightly more pronounced in subjects with LDL cholesterol above the median (143 mg/dl) but this did not achieve statistical significance (no effect-measure modification); (4) Associations of OxPL/apoB were present both for individual cardiovascular endpoints as well as composite endpoints when revascularization procedures and new onset peripheral arterial disease were included (FIG. 7). Similar data were noted for Lp(a) (FIG. 7); (5) The HR [95% CI] for CVD calculated for a 1-SD unit increase in loge-transformed OxPL/apoB level was 1.36[1.00-1.85] P=0.049 in subjects with low-molecular-weight apo(a) phenotypes ($\leq$22 Kringle-IV repeats) and 1.55[1.14-2.11]P=0.005 in subjects with high-molecular-weight apo(a) phenotypes (>22 Kringle-IV repeats) (P=0.48 for effect modification). There were no significant differences in any of the above analyses in men versus women.

Exploratory analysis to assess whether a J-shaped curve exists between OxPL/apoB and Lp(a) levels and CVD.

To further evaluate the relationship between OxPL/apoB or Lp(a) and CVD risk, hazard ratios were computed for sextile groups of given variables suggesting the presence of a J-shaped curve in the relationship of OxPL/apoB and Lp(a) and CVD (FIG. 6). However, this study was not adequately sized statistically to test the hypothesis that a J-shaped scale fits the data better than a linear dose-response relationship.

The examples set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining a subject's predisposition to a coronary artery disease, the method comprising:
    a) determining the subject's plasma OxPL level, wherein the OxPL is associated with apolipoprotein B-100 (apoB) particles;
    b) determining the subject's Lp-PLA$_2$ mass or activity; and
    c) correlating a) and b), wherein increased levels of OxPL and Lp-PLA$_2$ are indicative of a predisposition to the coronary artery disease.

2. The method of claim 1, further comprising determining the presence of a pro-inflammatory genotype in the IL-1 gene cluster of the subject.

3. The method of claim 2, wherein determining the IL-1 gene cluster genotype of the subject comprises identifying a pro-inflammatory single nucleotide polymorphism in the IL-1A, IL-1B, or IL-1B gene, or any combination thereof.

4. The method of claim 3, wherein the single nucleotide polymorphism in IL-1A is associated with the nucleotide at position +4845.

5. The method of claim 4, wherein the nucleotide at position +4845 is not G.

6. The method of claim 4, wherein the nucleotide at position +4845 is T.

7. The method of claim 3, wherein the single nucleotide polymorphism in IL-1B is associated with the nucleotide at position +3954.

8. The method of claim 7, wherein the nucleotide at position +3954 is not C.

9. The method of claim 7, wherein the nucleotide at position +3954 is T.

10. The method of claim 3, wherein the single nucleotide polymorphism in IL-1B is associated with the nucleotide at position −511.

11. The method of claim 10, wherein the nucleotide at position −511 is not C.

12. The method of claim 10, wherein the nucleotide at position −511 is T.

13. The method of claim 1, wherein the determination is independent of C-reactive protein activity.

14. The method of claim 1, wherein the subject is a human subject.

15. A method of identifying a subject having or at risk of having or developing a coronary artery disease , comprising
    (1) measuring in a sample from the subject at least:
        (a) Lp-PLA$_2$ or sPLA$_2$ activity or mass in the sample; and
        (b) oxidized phospholipids (OxPL) on apolipoprotein B-100 particles (apoB), and
    (2) correlating the measurements of (1) (a) and (1) (b) with a risk of having or developing a coronary artery disease.

16. A method of identifying a subject having or at risk of having or developing a coronary artery disease, comprising
    (1) measuring in a sample from the subject at least:
        (a) Lp-PLA$_2$ activity or mass in the sample, wherein the Lp-PLA$_2$ activity is measured in a fluorimetric assay comprising a substrate for Lp-PLA$_2$; and
        (b) oxidized phospholipids (OxPL) on apolipoprotein B-100 particles (apoB), and
    (2) correlating the measurements of (1)(a) and (1)(b) with a risk of having or developing a coronary artery disease.

* * * * *